(12) United States Patent
Deng et al.

(10) Patent No.: US 8,618,282 B2
(45) Date of Patent: Dec. 31, 2013

(54) PROCESS FOR PREPARING BENZOTHIAZEPINES FROM GAMMA-AMINOALKYLBENZENES

(75) Inventors: Shixian Deng, White Plains, NY (US); Sandro Belvedere, New York, NY (US); Jiaming Yan, New York, NY (US); Donald Landry, New York, NY (US)

(73) Assignee: Les Laboratoires Servier, Suresnes Cedex (FR)

( * ) Notice: Subject to any disclaimer, the term of this patent is extended or adjusted under 35 U.S.C. 154(b) by 912 days.

(21) Appl. No.: 12/397,212

(22) Filed: Mar. 3, 2009

(65) Prior Publication Data

US 2009/0227788 A1 Sep. 10, 2009

Related U.S. Application Data

(60) Provisional application No. 61/033,197, filed on Mar. 3, 2008.

(51) Int. Cl.
*C07D 281/08* (2006.01)
*C07D 281/10* (2006.01)

(52) U.S. Cl.
USPC ........................................................ 540/552

(58) Field of Classification Search
USPC ........................................................ 540/552
See application file for complete search history.

(56) References Cited

U.S. PATENT DOCUMENTS

| 5,416,066 A | 5/1995 | Kaneko et al. | 514/211 |
| 5,580,866 A | 12/1996 | Housley et al. | 514/211 |
| 2005/0215540 A1 | 9/2005 | Marks et al. | 514/211.09 |
| 2006/0194767 A1 | 8/2006 | Marks et al. | |
| 2007/0049572 A1 | 3/2007 | Marks et al. | 514/211.09 |
| 2007/0173482 A1 | 7/2007 | Marks et al. | 514/80 |

FOREIGN PATENT DOCUMENTS

| WO | WO 98/05657 A1 | 2/1998 |
| WO | WO 2005/037195 A2 | 4/2005 |

OTHER PUBLICATIONS

Boudet et al., "Recherches dans la série des thiazépines. Synthèse et étude de la benzo-6.7 tétrahydrothiazépine-1.4," C. R. Acad. Sc. Paris, vol. 282, pp. 249-251 (1976).
Katritzky et al., "Convenient syntheses of 2,3,4,5-tetrahydro-1,4-benzothiazepines, -1,4-benzoxazepines and -1,4-benzodiazepines," J. Chem. Soc., Perkin Trans. 1, 2002, 592-598.
Mishra et al., "Diversity-Oriented Synthetic Approach to Naturally Abundant S-Amino Acid Based Benzannulated Enantiomerically Pure Medium Ring Heterocyclic Scaffolds Employing Inter- and Intramolecular Mitsunobu Reactions," J. Comb. Chem., 2007, 9(2): 321-338.

International Search Report and the Written Opinion of the International Searching Authority, application No. PCT/US2009/035863, dated May 25, 2009.
Dieter Enders, et al., "Asymmetric Total Synthesis of the 1-*ept*-Aglycon of the Cripowellins A and B," J. Org. Chem. 2005. 70, 10538-10551.
Paola Manini, et al., "A Novel Octahydropyridobenzothiazepine Metabolite in Human Urine: Biomimetic Formation from the McLanogen 5-S-Cysteinyldopa and Formaldehyde via a Peculiar Sulfur-Controlled Double Pictet-Spengler Condensation," J. Org. Chem. 2000, 65, 4269-4273.
Lee, S.H., et al., "The direct conversion of carbamates to areas using aluminum amides," Tetrahedran 2004, 60, 3439-3443.
Vauthey, L., et al., "An environmentally benign access to carbamates and ureas," Tetrahedron Lett., 2000, 41, 6347-6350.
Han, C., and Porco, J.A., "Synthesis of Carbamates and Ureas Using Zr(IV)-Cataluzed Exchanged Processes," Organic Lett., 2007, 9, 1517-1520.

*Primary Examiner* — Brenda Coleman
(74) *Attorney, Agent, or Firm* — Hueschen and Sage

(57) ABSTRACT

The invention provides a process for preparing a 2,3,4,5-tetrahydro[1,4]benzothiazepine of formula:

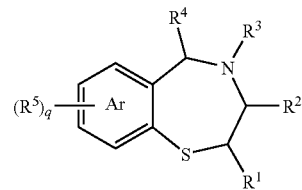

by reacting a [2-(acylaminoethyl)thio]arene of formula

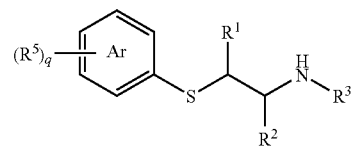

with an aldehyde or a multimer thereof, and with an acid. The invention also provides for first reacting the [2-(acylaminoethyl)thio]arene with the aldehyde or multimer thereof and a base to form an [N-hydroxymethyl-2-[acylaminoethyl)thio] arene of formula

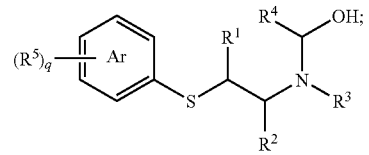

then treating the [N-hydroxymethyl-2-(acylaminoethyl)thio] arene with the acid to form the 2,3,4,5-tetrahydro[1,4]benzothiazepine.

33 Claims, No Drawings

PROCESS FOR PREPARING BENZOTHIAZEPINES FROM GAMMA-AMINOALKYLBENZENES

This application claims the benefit of application 61/033,197 filed Mar. 3, 2008.

FIELD OF THE INVENTION

The invention relates to processes for preparing 2,3,4,5-tetrahydrobenzo[1,4]thiazepines from the corresponding [2-(acylaminoethyl)thio]arenes.

BACKGROUND OF THE INVENTION 2,3,4,5-tetrahydrobenzo[f][1,4]thiazepines are important compounds because of their biological activities, as disclosed, for example, in U.S. Pat. Nos. 5,416,066 and 5,580,866 and published US Patent Applications Nos. 2005/0215540, 2007/0049572 and 2007/0173482.

Synthetic procedures exist for the preparation of 2-oxo-, 3-oxo-, 5-oxo- and 3,5-dioxo-1,4-benzothiazepines and for 2,3-dihydro-1,4-benzothiazepines. However, relatively few publications describe the preparation of 2,3,4,5-tetrahydrobenzo-1,4-thiazepines that contain no carbonyl groups, and most of these involve reduction of a carbonyl group or an imine. Many of the routes described in the literature proceed from an ortho-substituted arene and use the ortho substituents as "anchors" for the attachment of the seven-membered ring. Essentially all the preparatively useful syntheses in the literature that do not begin with an ortho-substituted arene employ a modification of the Bischler-Napieralski reaction in which the carbon of the acyl group on the γ-amide becomes the carbon adjacent the bridgehead and the acyl substituent becomes the 5-substituent. Like earlier mentioned syntheses, the Bischler-Napieralski synthesis requires reduction of an iminium intermediate.

It would be useful to have an intramolecular reaction for the direct construction of 2,3,4,5-tetrahydrobenzo[1,4]thiazepines that would allow more flexibility in the 4- and 5-substituents and that would avoid a separate reduction step. The Pictet Spengler reaction, in which a β-arylethylamine such as tryptamine undergoes 6-membered ring closure after condensation (cyclization) with an aldehyde, has been widely used in the synthesis of 6-membered ring systems over the past century and might be contemplated for this purpose. The Pictet Spengler reaction, however, has not been generally useful for 7-membered ring systems such as 1,4-benzothiazepines. A plausible explanation is that the failure of the reaction for typical arenes was due to the unfavorable conformation of the 7-membered ring. There are two isolated examples of an intramolecular Pictet-Spengler-type reaction producing a good yield of a benzothiazepine from the addition of formaldehyde. In one case, the starting material was a highly unusual activated arene (a catechol derivative) [Manini et al. *J. Org. Chem.* (2000), 65, 4269-4273]. In the other case, the starting material is a bis(benzotriazolylmethyl)amine that cyclizes to a mono(benzotriazolyl)benzothiazole [Katritzky et al. *J. Chem. Soc. P1* (2002), 592-598].

SUMMARY OF THE INVENTION

In the present invention, it has been unexpectedly found that, when a functional group such as an amide, urea or carbamate is introduced onto the primary amine, seven-membered rings can be prepared in high yield in a single step. Moreover, the acyl group can be readily removed to allow elaboration at position 4.

The invention relates to a process for preparing a 2,3,4,5-tetrahydrobenzo[f][1,4]benzothiazepine of formula:

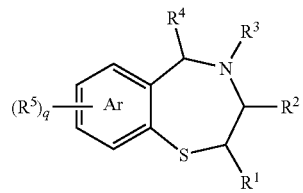

In one aspect, the process comprises reacting a [2-(acylaminoethyl)thio]arene of formula

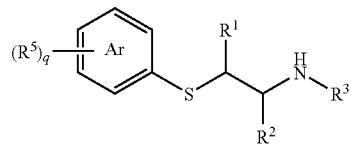

with an aldehyde of formula $R^4CHO$ or a multimer thereof, and with an acid. In these formulae, Ar is a monocyclic, bicyclic or tricyclic aryl or heteroaryl ring system;

$R^1$, $R^2$ and $R^4$ are each independently $H(C_1-C_{20})$hydrocarbon, $(C_1-C_6)$alkyl, cycloalkyl, aryl, heterocyclyl, heteroaryl, $(C_1-C_6)$alkyl-aryl, $(C_1-C_6)$alkyl-cycloalkyl, $(C_1-C_6)$alkyl-heterocyclyl or $(C_1-C_6)$alkyl-heteroaryl, each of the aryl, cycloalkyl, heterocyclyl and heteroaryl optionally substituted with one to three substituents independently selected from the group consisting of halogen, alkyl, alkoxyl, nitro, cyano and haloalkyl;

$R^3$ is $(C_1-C_{10})$acyl; $P(O)R^8R^9$, $C(=O)$—$R^{10}$, $C(=S)$—$R^{11}$, $S(=O)_2R^{12}$, $(CH_2)_mR^{13}$, a nitrogen protecting group, OH, $(C_1-C_6)$alkyl, cycloalkyl, aryl, heterocyclyl, heteroaryl, $(C_1-C_6)$alkyl-aryl, $(C_1-C_6)$alkyl-cycloalkyl, $(C_1-C_6)$alkyl-heterocyclyl or $(C_1-C_6)$alkyl-heteroaryl, each of the aryl, cycloalkyl, heterocyclyl and heteroaryl optionally substituted with one to three substituents independently selected from the group consisting of halogen, alkyl, alkoxyl, nitro, cyano and haloalkyl; or, taken together, $R^2$ and $R^3$ form an oxo-substituted nitrogen-containing heterocycle;

$R^5$ is independently in each of its occurrences H, $(C_1-C_{20})$ hydrocarbon, $(C_1-C_6)$alkyl, cycloalkyl, aryl, heterocyclyl, heteroaryl, $(C_1-C_6)$alkyl-aryl, $(C_1-C_6)$alkyl-cycloalkyl, $(C_1-C_6)$alkyl-heterocyclyl or $(C_1-C_6)$alkyl-heteroaryl, halogen, acyl, $SO_3$, —$OR^6$, —$SR^6$, —$NR^{6a}R^{6b}$, —$N(R^6)C(=O)OR^7$, $N(R^6)C(=O)R^7$, —$C(=O)NR^{6a}R^{6b}$, —$C(=O)OR^6$, —$C(=O)R^6$—$OC(=O)R^6$—$NO_2$, —CN, —$(C_1-C_6)$haloalkyl, —O—$(C_1-C_6)$haloalkyl, —$N_3$ or —$P(O)R^8R^9$, each of the aryl, cycloalkyl, heterocyclyl and heteroaryl optionally substituted with one to three substituents independently selected from the group consisting of halogen, alkyl, alkoxyl, nitro, cyano and haloalkyl;

$R^{10}$ and $R^{11}$ are each independently H, —$OR^{14}$, —$NR^{6a}R^{6b}$, NHNHR$^{15}$, NHOH, $CONH_2NHR^{15}$, $CO_2R^{15}$, $CONR^{15}$, halogen, alkoxy, aryloxy, allyloxy, benzyloxy, substituted benzyloxy, fluoroenylmethoxy, adamantyloxy, $(C_1-C_{20})$hydrocarbon, $(C_1-C_6)$alkyl, cycloalkyl, aryl, heterocyclyl, heteroaryl, $(C_1-C_6)$alkyl-aryl, $(C_1-C_6)$alkyl-cycloalkyl, ($C_1$-$C_6$)alkyl-heterocyclyl or ($C_1$-$C_6$)alkyl-heteroaryl, each of the aryl, cycloalkyl, heterocyclyl and heteroaryl optionally substituted with one to three substituents independently selected from the group consisting of halogen, alkyl, alkoxyl, nitro, cyano and haloalkyl;

$R^{6a}$, $R^{6b}$, $R^{12}$, $R^{14}$, $R^{15}$, $R^{16}$ and $R^{17}$ are each independently at each of their occurrences H, —$OR^{15}$, —$NR^{15}R^{16}$, $NHNHR^{16}$, NHOH, ($C_1$-$C_{20}$)hydrocarbon, ($C_1$-$C_6$)alkyl, cycloalkyl, aryl, heterocyclyl, heteroaryl, ($C_1$-$C_6$)alkyl-aryl, ($C_1$-$C_6$)alkyl-cycloalkyl, ($C_1$-$C_6$)alkyl-heterocyclyl or ($C_1$-$C_6$)alkyl-heteroaryl, each of the aryl, cycloalkyl, heterocyclyl and heteroaryl optionally substituted with one to three substituents independently selected from the group consisting of halogen, alkyl, alkoxyl, nitro, cyano and haloalkyl, or $R^{6a}$ and $R^{6b}$, together with the nitrogen to which they are attached, represent a 5, 6, or 7-membered ring nitrogen-containing heterocycle;

$R^{13}$ is $NH_2$, OH, —$SO_2R^{16}$, —$NHSO_2R^{16}$, C(=O)$R^{17}$, NH(C=O)$R^{17}$, —O(C=O)$R^{17}$, or —P(O)$R^8R^9$; m is an integer from 1-10; and q is zero or an integer from 1-4, provided that when $R^5$ is —C(=O)$R^6$, $R^5$ is not in an ortho position relative to the sulfur side chain.

Advantageously, $R^3$ is acetyl, benzoyl, toluoyl, benzyloxycarbonyl, t-butoxycarbonyl, acryloyl, oxalyl or —C(=O) $NR^{6a}R^{6b}$, $R^5$ is ($C_1$-$C_4$)hydrocarbon, halogen, —$OR^6$, —$SR^6$, —$NO_2$, —CN, —($C_1$-$C_4$)haloalkyl or —O—($C_1$-$C_4$) haloalkyl; and $R^6$ is H or ($C_1$-$C_6$)hydrocarbon. Also, Ar is preferably phenyl.

Alternatively, $R^2$ and $R^3$ taken together form a pyrrolidone, oxazolidinone or piperidinone. In another embodiment, $R^1$, $R^2$ and $R^4$ are hydrogen.

In another aspect of the invention, the [2-(acylaminoethyl) thio]arene may first be reacted with the aldehyde and a base to form an [N-hydroxymethyl-2-[acylaminoethyl)thio]arene of formula

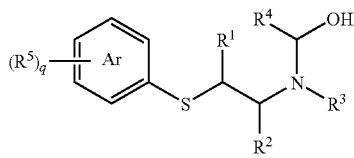

and then the [N-hydroxymethyl-2-(acylaminoethyl)thio] arene is treated with an acid to form the 2,3,4,5-tetrahydrobenzo[f][1,4]thiazepine.

In both aspects of the invention, the acid may be a sulfonic acid such as, for example, toluenesulfonic acid, benzenesulfonic acid, methanesulfonic acid, pyridinium p-toluenesulfonate, or trifluoromethanesulfonic acid) or a Lewis acid such as, for example, boron trifluoride etherate, titanium tetrachloride, aluminum chloride or zinc chloride, and the preferred aldehyde or multimer is formaldehyde, paraformaldehyde or 1,3,5-trioxane. In the second aspect of the invention, the base may be one or more of an alkali metal hydride, hydroxide or carbonate, pyridine, or a trialkylamine. Examples of bases include, but are not limited to, NaH, NaOH, KOH, $Na_2CO_3$, $K_2CO_3$, $Cs_2CO_3$, $Et_3N$ or $(iPr)_2NEt$.

In a preferred embodiment of the invention, when $R^3$ is ($C_1$-$C_{10}$)acyl of formula —C(=O)—$R^{18}$, or a nitrogen protecting group, OH, wherein $R^{18}$ is H, ($C_1$-$C_6$)alkyl, ($C_1$-$C_6$) alkoxy, allyloxy, benzyloxy, substituted benzyloxy, fluorenylmethoxy or adamantyloxy, a compound of formula

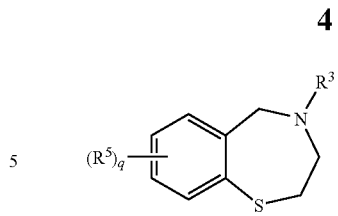

is converted to an oxalate compound of formula

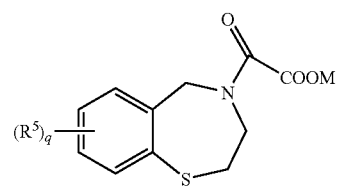

where M can be H, ammonium, alkali metal or alkaline earth metal. In this particular embodiment, q is 0 or 1; $R^1$, $R^2$ and $R^4$ are hydrogen; $R^3$ is ($C_1$-$C_{10}$)acyl of formula —C(=O)—$R^{18}$, wherein $R^{18}$ is H, ($C_1$-$C_6$)alkyl, ($C_1$-$C_6$)alkoxy, allyloxy, benzyloxy, substituted benzyloxy, fluorenylmethoxy or adamantyloxy; $R^5$ is H, ($C_1$-$C_4$)hydrocarbon, halogen, —$OR^6$, —$SR^6$, —$NO_2$, —CN, —($C_1$-$C_4$)haloalkyl or —O—($C_1$-$C_4$) haloalkyl; and $R^6$ is H or ($C_1$-$C_6$)hydrocarbon.

The conversion step typically comprises cleaving the $R^3$ group to provide a 2,3,4,5-tetrahydrobenzo[f][1,4]thiazepine of formula

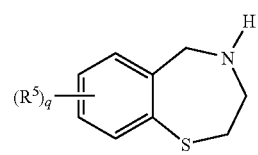

acylating the 2,3,4,5-tetrahydrobenzo[f][1,4]thiazepine with an oxalate ester; and then hydrolyzing the ester. In one embodiment, the hydrolysis step comprises treating the ester with a base of the type utilized above, and, optionally when M is H, acidifying. When M is H, the oxalate compound can be further converted into a salt thereof, wherein M is an alkali or alkaline earth cation such as $Na^+$, $Mg^{++}$ or $Ca^{++}$, or M is an ammonium, such as $NH_4^+$.

In a specific embodiment, wherein q is 1 and $R^5$ is $OCH_3$ at position 7 of the benzothiazepine ring, the compound has the formula

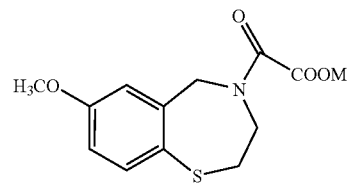

In this specific embodiment, M may be hydrogen, an alkali metal, an alkaline earth metal or ammonium.

In another embodiment of the invention, a compound of the formula

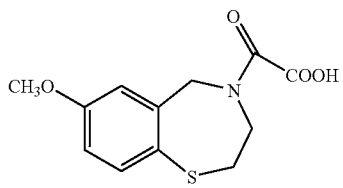

is specifically obtained beginning with an [2-(acylaminoethyl)thio]arene with the formula

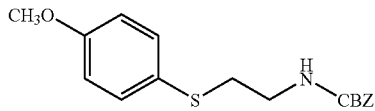

In this embodiment, the aldehyde is paraformaldehyde and the acid is toluenesulfonic acid or hydrochloric acid. The reaction provides a CBZ-protected benzothiazepine of formula

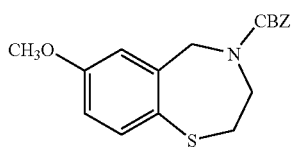

This method further comprises cleaving the carbobenzyloxy group with acid to provide 7-methoxy-2,3,4,5-tetrahydrobenzo[f][1,4]thiazepine; acylating the 7-methoxy-2,3,4,5-tetrahydrobenzo[f][1,4]thiazepine with methyl chlorooxalate; hydrolyzing the methyl ester with aqueous base; acidifying to form the acid compound; and optionally converting the acid compound to a compound of formula

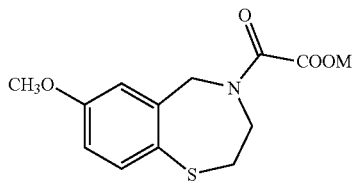

In this embodiment, M is ammonium, an alkali metal or an alkaline earth metal.

In another embodiment of the invention, the 2,3,4,5-tetrahydro[1,4]benzothiazepine is prepared by treating a [2-(acylaminoethyl)thio]arene of formula

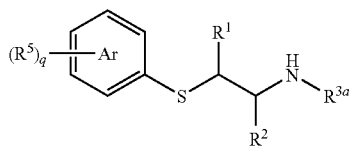

with an aldehyde of formula $R^4CHO$ or a multimer thereof, nd an acid to produce a compound of formula

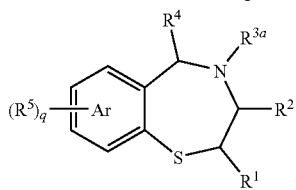

In this embodiment, $R^3$ is $R^{3a}$ wherein $R^{3a}$ is $(C_1-C_{10})$acyl of formula —C(=O)—$R^{18}$, wherein $R^{18}$ is H, $(C_1-C_6)$alkyl, $(C_1-C_6)$alkoxy, allyloxy, benzyloxy, substituted benzyloxy, fluorenylmethoxy or adamantyloxy.

The $R^{3a}$ substituent is further cleaved to produce a 4-unsubstituted-2,3,4,5-tetrahydrobenzo[f][1,4]thiazepine of formula

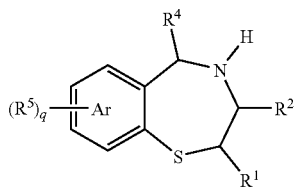

The 4-unsubstituted-2,3,4,5-tetrahydrobenzo[f][1,4]thiazepine is acylated with $R^3X$ to produce a compound of formula

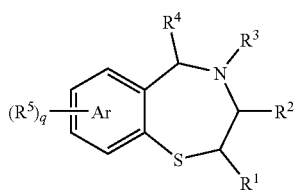

In this embodiment, $R^3$ is $(C_1-C_{10})$acyl, $P(O)R^8R^9$, C(=O)—$R^{10}$, C(=S)—$R^{11}$, S(=O)$_2R^{12}$, $(CH_2)_mR^{13}$, a nitrogen protecting group, OH, $(C_1-C_6)$alkyl, cycloalkyl, aryl, heterocyclyl, heteroaryl, $(C_1-C_6)$alkyl-aryl, $(C_1-C_6)$alkyl-cycloalkyl, $(C_1-C_6)$alkyl-heterocyclyl or $(C_1-C_6)$alkyl-heteroaryl, each of the aryl, cycloalkyl, heterocyclyl and heteroaryl optionally substituted with one to three substituents independently selected from the group consisting of halogen, alkyl, alkoxyl, nitro, cyano and haloalkyl; or, taken together, $R^2$ and $R^3$ form an oxo-substituted nitrogen-containing heterocycle; and X is halogen, $(C_1-C_{10})$acyloxy, or an activated ester residue. In a specific embodiment, $R^3$ is t-butoxycarbonyl, benzyloxycarbonyl, substituted benzyloxycarbonyl or fluorenylmethoxycarbonyl. In another embodiment, $R^3X$ is an acid chloride, an acid anhydride, an activated ester, a chloroformate or a carbamic chloride.

In another embodiment of the invention, the compound of formula

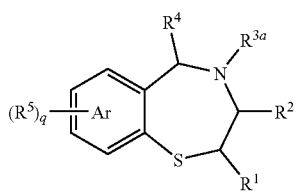

wherein Ar, $R^1$, $R^2$, $R^4$, $R^5$ and q are as defined above, and $R^{3a}$ is —C(=O)—$R^{18}$ wherein $R^{18}$ is $(C_1-C_4)$alkoxy, allyloxy, benzyloxy, substituted benzyloxy, fluorenylmethoxy or adamantyloxy; is reacted with an amine of formula HN(R$^{19}$)$_2$, to form a compound of formula

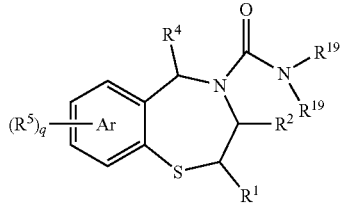

wherein each R$^{19}$ is independently chosen from H and (C$_1$-C$_6$)alkyl, or taken together, N(R$^{19}$)$_2$ represents a 5, 6, or 7-membered ring nitrogen-containing heterocycle. The 5, 6, or 7-membered ring nitrogen-containing heterocycle may be, for example, pyrrolidine, piperidine, morpholine, 4-CBZpiperazine or azepan.

In another preferred embodiment of the invention, when the [2-(acylaminoethyl)thio]arene compound has the formula

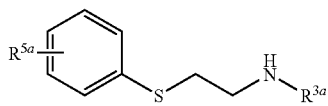

it can be reacted with formaldehyde or a multimer thereof and an acid to form a protected benzothiazepine of the formula

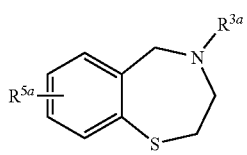

or it can be reacted with formaldehyde or a multimer thereof and a base to form an [N-hydroxymethyl-2-(acylaminoethyl)thio]benzene of formula

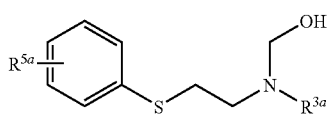

The [N-hydroxymethyl-2-(acylaminoethyl)thio]benzene may further be reacted with an acid to provide a protected benzothiazepine of formula

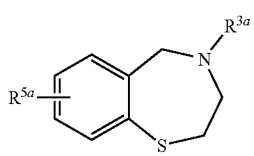

wherein R$^{3a}$ is (C$_1$-C$_{10}$)acyl of formula —C(=O)—R$^{18}$; R$^{5a}$ is H, (C$_1$-C$_4$)hydrocarbon, halogen, —OR$^6$, —SR$^6$, —NO$_2$, —CN, —(C$_1$-C$_4$)haloalkyl or —O—(C$_1$-C$_4$)haloalkyl; R$^6$ is H or (C$_1$-C$_6$)hydrocarbon; and R$^{18}$ is H, (C$_1$-C$_6$)alkyl, (C$_1$-C$_4$)alkoxy, allyloxy, benzyloxy, substituted benzyloxy, fluorenylmethoxy or adamantyloxy.

The R$^{3a}$ group can be further cleaved to obtain a compound of formula

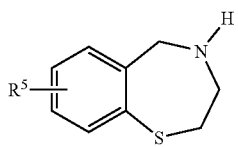

The 4-unsubstituted 2,3,4,5-tetrahydrobenzo[f][1,4]thiazine may be acylated with R$^3$X to obtain a compound of formula

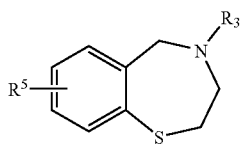

where R$^3$ is (C$_1$-C$_{10}$)acyl; and X is halogen, (C$_1$-C$_{10}$)acyloxy, or an activated ester residue.

In another embodiment, the compound of formula

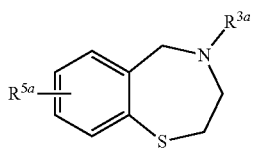

is further converted to

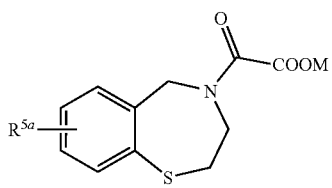

where M is H, ammonium, an alkali metal or an alkaline earth metal.

In this embodiment, conversion is accomplished by cleaving the R$^{3a}$ group to provide a 2,3,4,5-tetrahydrobenzo[f][1,4]thiazepine, acylating the 2,3,4,5-tetrahydrobenzo[f][1,4]thiazepine with an oxalate ester, and hydrolyzing the ester. In one embodiment, the hydrolyzing step comprises treating the ester with a base and, optionally, when M is H, acidifying. Optionally, the resulting product is converted wherein M is H into a salt thereof, wherein M is a cation such as an alkali metal, an alkaline earth metal or an ammonium.

In a third aspect of the invention, the [2-(acylaminoethyl)thio]arene is obtained by reacting a compound of formula

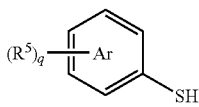

with a compound of formula

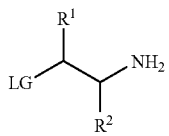

to provide a compound of formula

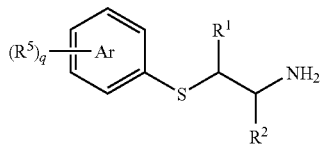

followed by a reaction with a compound of formula $R^3X$. A base can be optionally used. LG is a leaving group for nucleophilic displacement by thiol and X is a leaving group for nucleophilic displacement by an amine. LG may be a halogen such as, for example, chloro, iodo or bromo, or a sulfonate such as, for example, methanesulfonate, toluenesulfonate, benzenesulfonate, trifluoromethanesulfonate, nitrophenylsulfonate or bromophenylsulfonate. $R^3X$ is typically an acid chloride, an acid anhydride, an activated ester, a chloroformate or a carbamic chloride.

In yet another aspect of the invention, the [2-(acylaminoethyl)thio]arene is prepared by reacting a compound of formula

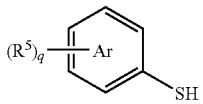

with a compound of formula

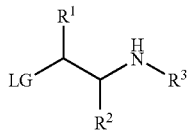

A base may optionally be used. LG is a leaving group for nucleophilic displacement by a thiol and can be a halogen (such as, for example, chloro, iodo and bromo) or a sulfonate (such as, for example, methanesulfonate, toluenesulfonate, benzenesulfonate, trifluoromethanesulfonate, nitrophenylsulfonate and bromophenylsulfonate).

DETAILED DESCRIPTION OF THE PREFERRED EMBODIMENTS

The invention relates to processes for preparing aryl-fused tetrahydrothiazepines, such as 2,3,4,5-tetrahydrobenzo[f][1,4]thiazepines.

Definitions

Throughout this specification the terms and substituents retain their definitions.

Alkyl is intended to include linear, branched, or cyclic hydrocarbon structures and combinations thereof. Lower alkyl refers to alkyl groups of from 1 to 6 carbon atoms. Examples of lower alkyl groups include methyl, ethyl, propyl, isopropyl, butyl, s- and t-butyl and the like. Preferred alkyl groups are those of $C_{20}$ or below. Cycloalkyl is a subset of alkyl and includes cyclic hydrocarbon groups of from 3 to 8 carbon atoms. Examples of cycloalkyl groups include c-propyl, c-butyl, c-pentyl, norbornyl and the like.

$C_1$ to $C_{20}$ hydrocarbon includes alkyl, cycloalkyl, polycycloalkyl, alkenyl, alkynyl, aryl and combinations thereof. Examples include benzyl, phenethyl, cyclohexylmethyl, camphoryl and naphthylethyl. The term "carbocycle" is intended to include ring systems consisting entirely of carbon but of any oxidation state. Thus $(C_3-C_{10})$ carbocycle refers to such systems as cyclopropane, benzene and cyclohexene; $(C_8-C_{12})$ carbopolycycle refers to such systems as bornane, decalin, indane and naphthalene.

Alkoxy or alkoxyl refers to groups of from 1 to 8 carbon atoms of a straight, branched, cyclic configuration and combinations thereof attached to the parent structure through an oxygen. Examples include methoxy, ethoxy, propoxy, isopropoxy, cyclopropyloxy, cyclohexyloxy and the like. Lower-alkoxy refers to groups containing one to four carbons. Methoxy is preferred. For the purpose of this application, alkoxy and lower alkoxy include methylenedioxy and ethylenedioxy.

Oxoalkyl refers to alkyl residues in which one or more carbons has been replaced by oxygen. Examples include methoxypropoxy, 3,6,9-trioxadecyl and the like.

Acyl refers to a substituent that is attached through —C(=O)— and that contains from one to ten carbons. The group may also contain heteroatoms such as oxygen and nitrogen. In one embodiment, acyl refers to formyl and to groups containing from 1 to 10 carbon atoms of a straight, branched, cyclic configuration, saturated, unsaturated and aromatic and combinations thereof, attached to the parent structure through a carbonyl functionality. One or more carbons in the acyl residue may be replaced by nitrogen, oxygen or sulfur as long as the point of attachment to the parent remains at the carbonyl. Examples include acetyl, benzoyl, propionyl, isobutyryl, t-butoxycarbonyl, benzyloxycarbonyl, —C(=O)NH₂ and the like. Lower-acyl refers to groups containing one to four carbons. Examples of $(C_1-C_{10})$acyl also include toluoyl, benzyloxycarbonyl, t-butoxycarbonyl, acryloyl, oxalyl and —C(=O)N(R¹¹)₂, wherein each R¹¹ is independently H or $(C_1-C_6)$alkyl, or taken together, N(R¹¹)₂ represents a 5, 6, or 7-membered ring nitrogen-containing heterocycle. The 5, 6, or 7-membered ring nitrogen-containing heterocycle may be, for example, pyrrolidine, piperidine, morpholine, 4-CBZpiperazine or azepan. The person of skill will recognize that the groups —C(=O)N(R¹¹)₂, together with the ring nitrogen to which they are attached, might also be named as ureas. In certain embodiments, other $(C_1-C_{10})$ acyl groups, described in *Protective Groups in Organic Synthesis* by T. W. Greene and P. G. M. Wuts [John Wiley & Sons, New York, 1999], may also be contemplated.

Aryl (Ar) and heteroaryl mean a 5- or 6-membered aromatic or heteroaromatic ring containing 0-3 heteroatoms selected from O, N, or S; a bicyclic 9- or 10-membered aromatic or heteroaromatic ring system containing 0-3 heteroatoms selected from O, N, or S; or a tricyclic 13- or 14-membered aromatic or heteroaromatic ring system containing 0-3 heteroatoms selected from O, N, or S. The aromatic 6- to 14-membered carbocyclic rings include, e.g., benzene, naphthalene, indane, tetralin, and fluorene and the 5- to 10-membered aromatic heterocyclic rings include, e.g., imidazole, pyridine, indole, thiophene, benzopyranone, thiazole, furan, benzofuran, benzimidazole, quinoline, isoquinoline, quinoxaline, pyrimidine, pyrazine, tetrazole and pyrazole.

Arylalkyl refers to a substituent in which an aryl residue is attached to the parent structure through alkyl. Examples are benzyl, phenethyl and the like. Heteroarylalkyl refers to a substituent in which a heteroaryl residue is attached to the parent structure through alkyl. Examples include, e.g., pyridinylmethyl, pyrimidinylethyl and the like.

Heterocycle means a cycloalkyl or aryl residue in which from one to three carbons is replaced by a heteroatom selected from the group consisting of N, O and S. The nitrogen and sulfur heteroatoms may optionally be oxidized, and the nitrogen heteroatom may optionally be quaternized. Examples of heterocycles that fall within the scope of the invention include pyrrolidine, pyrazole, pyrrole, tetrahydroisoquinoline, benzodioxan, benzodioxole (commonly referred to as methylenedioxyphenyl, when occurring as a substituent), tetrazole, morpholine, thiazole, pyridine, pyridazine, pyrimidine, thiophene, furan, oxazole, oxazoline, isoxazole, dioxane, tetrahydrofuran and the like. It is to be noted that heteroaryl is a subset of heterocycle in which the heterocycle is aromatic.

Substituted alkyl, aryl, cycloalkyl, heterocyclyl and so on refer to alkyl, aryl, cycloalkyl, or heterocyclyl wherein up to three H atoms in each residue are replaced with halogen, haloalkyl, hydroxy, lower alkoxy, carboxy, carboalkoxy (also referred to as alkoxycarbonyl), carboxamido (also referred to as alkylaminocarbonyl), cyano, carbonyl, nitro, amino, alkylamino, dialkylamino, mercapto, alkylthio, sulfoxide, sulfone, acylamino, amidino, phenyl, benzyl, heteroaryl, phenoxy, benzyloxy, or heteroaryloxy.

The term "halogen" means fluorine, chlorine, bromine or iodine.

Terminology related to "protecting", "deprotecting" and "protected" functionalities occurs throughout this application. Such terminology is well understood by persons of skill in the art and is used in the context of processes which involve sequential treatment with a series of reagents. In that context, a protecting group refers to a group which is used to mask a functionality during a process step in which it would otherwise react, but in which reaction is undesirable. The protecting group prevents reaction at that step, but may be subsequently removed to expose the original functionality. The removal or "deprotection" occurs after the completion of the reaction or reactions in which the functionality would interfere. Thus, when a sequence of reagents is specified, as it is in the processes of the invention, the person of ordinary skill can readily envision those groups that would be suitable as "protecting groups".

In the case of the present invention, the functionalities that must be protected include amines, and occasionally carboxylic acids and alcohols. Suitable groups for that purpose are discussed in standard textbooks in the field of chemistry, such as *Protective Groups in Organic Synthesis* by T. W. Greene and P. G. M. Wuts [John Wiley & Sons, New York, 1999], which is incorporated herein by reference. Particular attention is drawn to the chapter titled "Protection for the Amino Group" (pages 494-614).

The abbreviations Me, Et, Ph, Tf, Ts and Ms represent methyl, ethyl, phenyl, trifluoromethanesulfonyl, toluenesulfonyl and methanesulfonyl, respectively. A comprehensive list of abbreviations utilized by organic chemists (i.e. persons of ordinary skill in the art) appears in the first issue of each volume of the Journal of Organic Chemistry. The list, which is typically presented in a table entitled "Standard List of Abbreviations" is incorporated herein by reference. As understood by one skilled in the art, the terms "isopropanol", "isopropyl alcohol" and "2-propanol" are equivalent and represented by CAS Registry No: 67-63-0.

An example of an acid which can be used in the processes of the invention include without limitation a sulfonic acid or a Lewis acid. An example of a sulfonic acid includes without limitation toluenesulfonic acid, benzenesulfonic acid, methanesulfonic acid, trifluoromethanesulfonic acid. An example of a Lewis acid includes without limitation boron trifluoride etherate, titanium tetrachloride, aluminum chloride or zinc chloride. An example of an acid salt is pyridinium p-toluenesulfonate.

An example of a base which can be used in the processes of the invention include without limitation an alkali metal hydride, a hydroxide or a carbonate, a pyridine or a trialkylamine. Specific bases include NaH, NaOH, KOH, $Na_2CO_3$, $K_2CO_3$, $Cs_2CO_3$, $Et_3N$ and $(iPr)_2NEt$.

Reference to an acid or base in the various embodiments set forth below include a reference to any of the above listed material.

The processes of the invention are shown in Scheme 1.

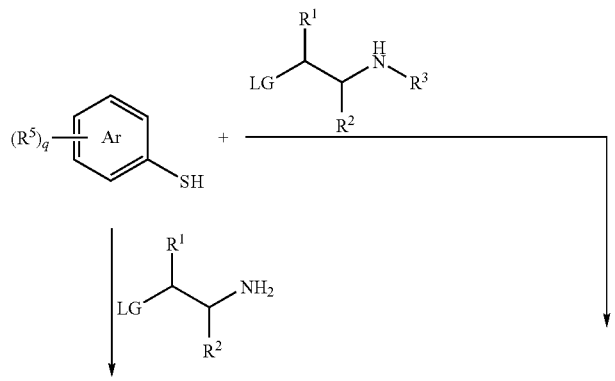

Scheme 1

-continued

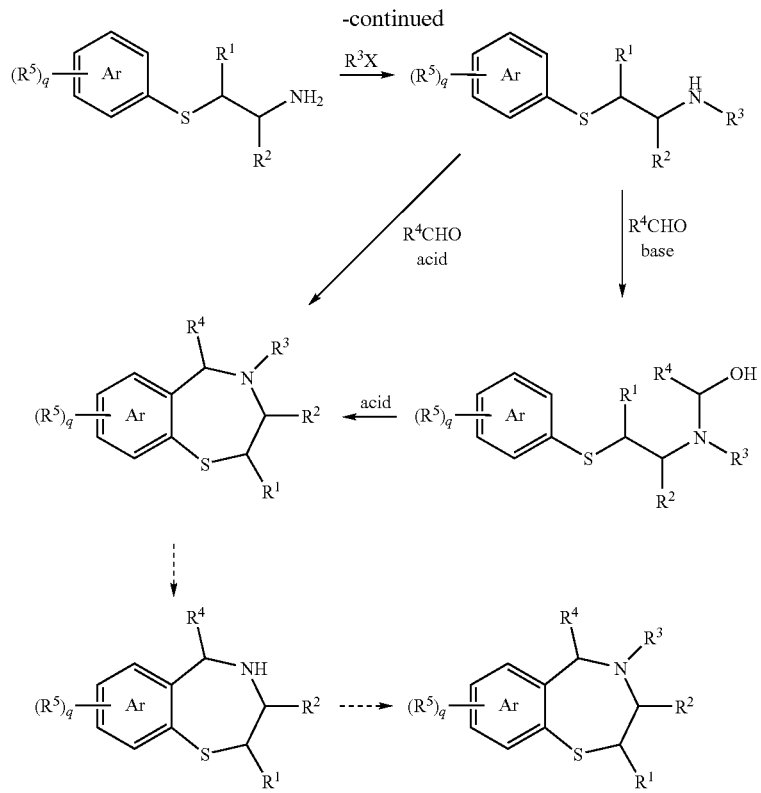

In a first aspect of the invention, the invention relates to a process for preparing a 2,3,4,5-tetrahydrobenzo[1,4]thiazepine of formula

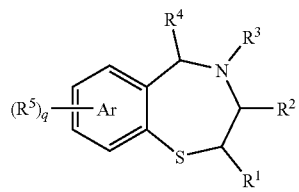

The process results in the formation of a thiazepine ring, and comprises treating a [2-(acylaminoethyl)thio]arene of formula

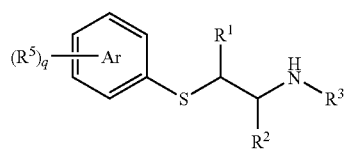

with an aldehyde of formula $R^4CHO$ or a multimer thereof, and an acid. In this process, Ar is a monocyclic, bicyclic or tricyclic aryl or heteroaryl ring system. Examples include compounds in which Ar is benzene (benzothiazepines) as well as compounds in which Ar is, for example naphthalene, pyridine or benzofuran.

$R^1$, $R^2$ and $R^4$ are each independently H, $(C_1-C_{20})$hydrocarbon, $(C_1-C_6)$alkyl, cycloalkyl, aryl, heterocyclyl, heteroaryl, $(C_1-C_6)$alkyl-aryl, $(C_1-C_6)$alkyl-cycloalkyl, $(C_1-C_6)$alkyl-heterocyclyl or $(C_1-C_6)$alkyl-heteroaryl, each of the aryl, cycloalkyl, heterocyclyl and heteroaryl optionally substituted with one to three substituents independently chosen from halogen, alkyl, alkoxyl, nitro, cyano and haloalkyl.

$R^3$ is $(C_1-C_{10})$acyl, $P(O)R^8R^9$, $C(=O)$—$R^{10}$, $C(=S)$—$R^{11}$, $S(=O)_2R^{12}$, $(CH_2)_mR^{13}$, a nitrogen protecting group, OH, $(C_1-C_6)$alkyl, cycloalkyl, aryl, heterocyclyl, heteroaryl, $(C_1-C_6)$alkyl-aryl, $(C_1-C_6)$alkyl-cycloalkyl, $(C_1-C_6)$alkyl-heterocyclyl or $(C_1-C_6)$alkyl-heteroaryl, each of the aryl, cycloalkyl, heterocyclyl and heteroaryl optionally substituted with one to three substituents independently selected from the group consisting of halogen, alkyl, alkoxyl, nitro, cyano and haloalkyl.

$R^5$ is independently in each of its occurrences H, $(C_1-C_{20})$ hydrocarbon, $(C_1-C_6)$alkyl, cycloalkyl, aryl, heterocyclyl, heteroaryl, $(C_1-C_6)$alkyl-aryl, $(C_1-C_6)$alkyl-cycloalkyl, $(C_1-C_6)$alkyl-heterocyclyl or $(C_1-C_6)$alkyl-heteroaryl, halogen, acyl, $SO_3$, —$OR^6$, $SR^6$, $NR^{6a}R^{6b}$, —$N(R^6)C(=O)OR^7$, $N(R^6)C(=O)R^7$, —$C(=O)NR^{6a}R^{6b}$, —$C(=O)OR^6$, —$C(=O)R^6$, —$OC(=O)R^6$, —$NO_2$, —$CN$, —$(C_1-C_6)$haloalkyl, —$O$—$(C_1-C_6)$haloalkyl, —$N_3$ or —$P(O)R^8R^9$, each of the aryl, cycloalkyl, heterocyclyl and heteroaryl optionally substituted with one to three substituents independently selected from the group consisting of halogen, alkyl, alkoxyl, nitro, cyano and haloalkyl.

$R^{10}$ and $R^{11}$ are each independently H, —$OR^{14}$, —$NR^{6a}R^{6b}$, $NHNHR^{15}$, $NHOH$, $CONH_2NHR^{15}$, $CO_2R^{15}$, $CONR^{15}$, halogen, alkoxy, aryloxy, allyloxy, benzyloxy, substituted benzyloxy, fluoroenylmethoxy, adamantyloxy, $(C_1-C_{20})$hydrocarbon, $(C_1-C_6)$alkyl, cycloalkyl, aryl, heterocyclyl, heteroaryl, $(C_1-C_6)$alkyl-aryl, $(C_1-C_6)$alkyl-cycloalkyl, $(C_1-C_6)$alkyl-heterocyclyl or $(C_1-C_6)$alkyl-heteroaryl, each of the aryl, cycloalkyl, heterocyclyl and heteroaryl optionally substituted with one to three substituents independently selected from the group consisting of halogen, alkyl, alkoxyl, nitro, cyano and haloalkyl.

$R^{6a}, R^{6b}, R^{12}, R^{14}, R^{15}, R^{16}$ and $R^{17}$ are each independently at each of their occurrences H, —$OR^{15}$, —$NR^{15}R^{16}$, $NHNHR^{16}$, NHOH, ($C_1$-$C_{20}$)hydrocarbon, ($C_1$-$C_6$)alkyl, cycloalkyl, aryl, heterocyclyl, heteroaryl, ($C_1$-$C_6$)alkyl-aryl, ($C_1$-$C_6$)alkyl-cycloalkyl, ($C_1$-$C_6$)alkyl-heterocyclyl or ($C_1$-$C_6$)alkyl-heteroaryl, each of the aryl, cycloalkyl, heterocyclyl and heteroaryl optionally substituted with one to three substituents independently selected from the group consisting of halogen, alkyl, alkoxyl, nitro, cyano and haloalkyl, or $R^{6a}$ and $R^{6b}$, together with the nitrogen to which they are attached, represent a 5, 6, or 7-membered ring nitrogen-containing heterocycle.

$R^{13}$ is $NH_2$, OH, —$SO_2R^{16}$, —$NHSO_2R^{16}$, $C(=O)R^{17}$, $NH(C=O)R^{17}$, —$O(C=O)R^{17}$, or —$P(O)R^8R^9$; m is an integer from 1-10; and q is zero or an integer from 1-4, provided that when $R^5$ is —$C(=O)R^6$, $R^5$ is not in an ortho position relative to the sulfur side chain.

As intended herein acyl refers to a substituent that is attached through —C(=O)— and that contains from one to ten carbons. The group may also contain heteroatoms such as oxygen and nitrogen. Examples of ($C_1$-$C_{10}$)acyl include acetyl, benzoyl, toluoyl, benzyloxycarbonyl, t-butoxycarbonyl, acryloyl, oxalyl and —$C(=O)N(R^{19})_2$, wherein each $R^{19}$ is hydrogen, alkyl, aryl, heterocyclyl, heteroaryl, alkylaryl, alkylheterocyclyl, or alkylheteroaryl, or taken together, $N(R^{19})_2$ represents a 5, 6, or 7-membered ring nitrogen-containing heterocycle. The 5, 6, or 7-membered ring nitrogen-containing heterocycle may be, for example, pyrrolidine, piperidine, morpholine, 4-CBZpiperazine or azepan. In a subset of $R^3$, $R^{3a}$ is ($C_1$-$C_{10}$)acyl of formula —C(=O)—$R^{18}$; and $R^{18}$ may be H, $C_1$-$C_4$ alkyl, ($C_1$-$C_4$)alkoxy, allyloxy, benzyloxy, substituted benzyloxy, fluorenylmethoxy or adamantyloxy. In certain embodiments, other ($C_1$-$C_{10}$)acyl groups, described in *Protective Groups in Organic Synthesis* by T. W. Greene and P. G. M. Wuts, may also be contemplated. The person of skill will recognize that the groups —C(=O)N($R^{19}$)$_2$, together with the ring nitrogen to which they are attached, might also be named as ureas.

As an alternative, $R^2$ and $R^3$ taken together may form an oxo-substituted nitrogen-containing heterocycle. Examples include a pyrrolidone, oxazolidinone or piperidinone. In these heterocycles the oxo will be adjacent the nitrogen, for example:

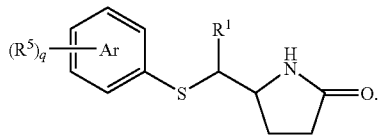

In the aldehyde component, $R^4$ may be H, ($C_1$-$C_6$)alkyl, aryl, heteroaryl, aryl($C_1$-$C_6$)alkyl and heteroaryl($C_1$-$C_6$)alkyl. Each of the aryl and heteroaryl residues may be optionally substituted with one to three substituents independently selected from halogen, alkyl, alkoxyl, nitro, cyano and haloalkyl. When $R^4$ is H, the aldehyde is formaldehyde. Formaldehyde itself is a gas, and therefore, it is often more easily manipulated as one of its commercially available oligomers and polymers, namely 1,3,5-trioxane and paraformaldehyde. Similarly, acetaldehyde may be employed as its commercially available trimer, paraldehyde (2,4,6-trimethyl-1,3,5-trioxane), or the aldehyde is paraformaldehyde. It will be clear to a person skilled in the art that a multimer of any aldehyde could be used in place of the aldehyde in the process of the invention.

The substituent(s) on the carbocycle, ($R^5$)$_q$, may be independently H, ($C_1$-$C_{10}$)hydrocarbon, halogen, —$OR^6$, —$SR^6$, —$N(R^6)_2$, —$N(R^6)C(=O)OR^7$, —$C(=O)N(R^6)_2$, —$C(=O)OR^6$, —$C(=O)R^6$, —$OC(=O)R^6$, —$NO_2$, —CN, —($C_1$-$C_6$)haloalkyl, —O—($C_1$-$C_6$)haloalkyl, —$N_3$ or —$P(O)R^8R^9$. In these substituents, $R^6$ may be H, ($C_1$-$C_{10}$) hydrocarbon, heterocyclyl, heterocyclyl($C_1$-$C_6$)alkyl or aryl ($C_1$-$C_6$)alkyl; $R^7$ may be ($C_1$-$C_{10}$)hydrocarbon, heterocyclyl, heterocyclylalkyl or arylalkyl; $R^8$ and $R^9$ may be independently H, ($C_1$-$C_{10}$)hydrocarbon, heterocyclyl, heterocyclyl ($C_1$-$C_6$)alkyl or aryl($C_1$-$C_6$)alkyl. In certain embodiments, $R^5$ may be H, ($C_1$-$C_4$)hydrocarbon, halogen, —$OR^6$—$SR^6$, —$NO_2$, —CN, —($C_1$-$C_4$)haloalkyl and —O—($C_1$-$C_4$)haloalkyl; and $R^6$ may be H or ($C_1$-$C_6$)hydrocarbon. When $R^5$ is —C(=O)$R^6$ and in the ortho position relative to the sulfur side chain, it may interfere with the desired reaction and produce lower yields of the thiazepine.

In a second aspect of the invention, the thiazepine ring is closed in two steps instead of one. The [2-(acylaminoethyl) thio]arene is reacted with the aldehyde set forth above and a base to form an [N-hydroxymethyl-2-(acylaminoethyl)thio] arene of formula

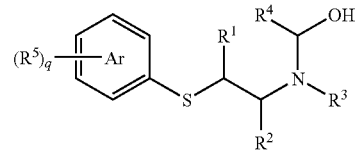

The [N-hydroxymethyl-2-(acylaminoethyl)thio]arene is treated with an acid to form the 2,3,4,5-tetrahydrobenzo[1,4] thiazepine. In one embodiment of the invention, when $R^3$ is ($C_1$-$C_{10}$)acyl of formula —C(=O)—$R^{18}$, or a nitrogen protecting group, OH, wherein $R^{18}$ is H, ($C_1$-$C_6$)alkyl, ($C_1$-$C_6$) alkoxy, allyloxy, benzyloxy, substituted benzyloxy, fluorenylmethoxy or adamantyloxy, the process comprises converting a compound of formula

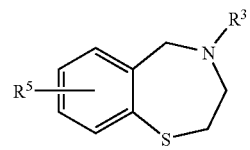

to a compound of formula

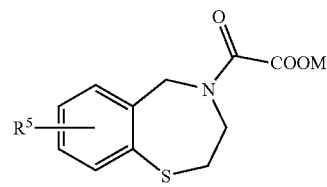

The conversion step is accomplished by cleaving the $R^3$ group to provide a 2,3,4,5-tetrahydrobenzo[f][1,4]thiazepine of formula

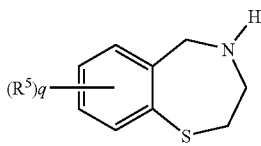
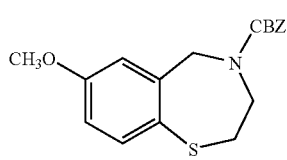

acylating the 2,3,4,5-tetrahydrobenzo[f][1,4]thiazepine with an oxalate ester; and removing the ester. In one embodiment, the ester is removed by hydrolysis. In accordance with this embodiment, hydrolysis is accomplished by treating the ester with a base or an acid. In another embodiment, however, when the ester includes a functional group cleavable by hydrogenation (e.g., benzyl ester), the benzyl or other cleavable group can be removed by catalytic hydrogenation, for example using $H_2$ and a metal catalyst such as Pd/C and Pt/C.

M can be H, ammonium, an alkali metal (e.g., sodium) or an alkaline earth metal (e.g., magnesium or calcium). The term "ammonium" is intended to include all species of cationic nitrogen compounds, including arginine, $NH_4^+$, $NalkylH_3^+$, $N(alkyl)_2H^+$, $N(alkyl)_3H^+$ and $N(alkyl)_4^+$.

It will be appreciated by a person of skill in the art that the compounds made by the processes of the present invention may be in hydrous form, e.g., monohydrate, dehydrate, trihydrate and the like, or they may be in anhydrous form. Similarly, the compounds made by the processes of the present invention may be in the form of a solvate with an organic solvent such as an alcohol, for example methanolate, ethanolate, and the like.

In one embodiment, the process is carried out as described above employing materials in which $R^1$, $R^2$ and $R^4$ are hydrogen and $R^3$ is COOR. The resulting ester is cleaved to produce the acid, which can optionally be converted to its salts wherein M is as described above. In a currently preferred embodiment, M is sodium.

In another embodiment of the invention, the process comprises preparing a compound of formula

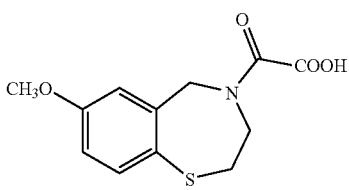

wherein the [2-(acylaminoethyl)thio]arene has the formula

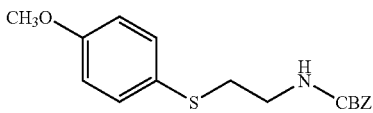

the aldehyde is paraformaldehyde and the acid is toluenesulfonic acid or hydrochloric acid and the reaction provides a CBZ-protected benzothiazepine of formula The carbobenzyloxy group is cleaved with an acid to provide 7-methoxy-2,3,4,5-tetrahydrobenzo[f][1,4]thiazepine which is acylated with methyl chlorooxalate. The methyl ester is hydrolyzed with an aqueous base; and then it is acidified to the acid compound.

The acid compound is optionally converted to a compound of formula

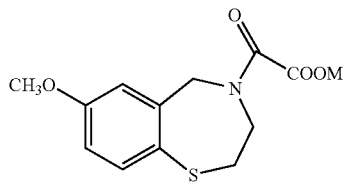

wherein M is ammonium, an alkali metal or an alkaline earth metal.

In another embodiment of the invention, when wherein $R^3$ is $R^{3a}$, the 2,3,4,5-tetrahydrobenzo[1,4]thiazepine is prepared by treating a [2-(acylaminoethyl)thio]arene of formula

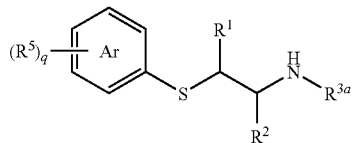

with an aldehyde of formula $R^4CHO$ or a multimer thereof, and an acid to produce a compound of formula

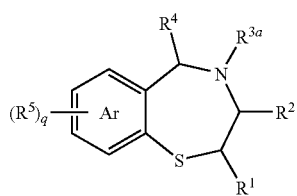

wherein $R^{3a}$ is $(C_1-C_{10})$acyl of formula —C(=O)—$R^{18}$ or a nitrogen protecting group, wherein $R^{18}$ is H, $(C_1-C_6)$alkyl, $(C_1-C_6)$alkoxy, allyloxy, benzyloxy, substituted benzyloxy, fluorenylmethoxy or adamantyloxy.

The $R^{3a}$ substituent can be further cleaved to produce a 4-unsubstituted-2,3,4,5-tetrahydrobenzo[f][1,4]thiazepine of formula

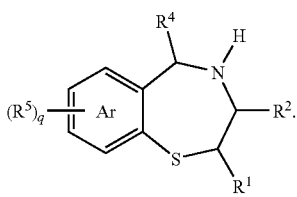

The 4-unsubstituted-2,3,4,5-tetrahydrobenzo[f][1,4]thiazepine is further acylated with $R^3X$ to produce a compound of formula

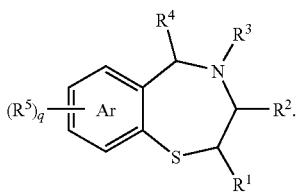

The substituent $R^3$ is $(C_1-C_{10})$acyl, $P(O)R^8R^9$, $C(=O)-R^{10}$, $C(=S)-R^{11}$, $S(=O)_2R^{12}$, $(CH_2)_mR^{13}$, a nitrogen protecting group, OH, $(C_1-C_6)$alkyl, cycloalkyl, aryl, heterocyclyl, heteroaryl, $(C_1-C_6)$alkyl-aryl, $(C_1-C_6)$alkyl-cycloalkyl, $(C_1-C_6)$alkyl-heterocyclyl or $(C_1-C_6)$alkyl-heteroaryl, each of the aryl, cycloalkyl, heterocyclyl and heteroaryl optionally substituted with one to three substituents independently selected from the group consisting of halogen, alkyl, alkoxyl, nitro, cyano and haloalkyl; and X is halogen, $(C_1-C_{10})$acyloxy, or an activated ester residue.

In a specific embodiment, the $R^3$ substituent is t-butoxycarbonyl, benzyloxycarbonyl, substituted benzyloxycarbonyl or fluorenylmethoxycarbonyl; and the $R^3X$ is an acid chloride, an acid anhydride, an activated ester, a chloroformate or a carbamic chloride.

In a specific embodiment, the [2-(acylaminoethyl)thio]arene compound has the formula

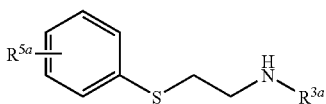

and can be reacted the formaldehyde or a multimer thereof and an acid to form a protected benzothiazepine of the formula

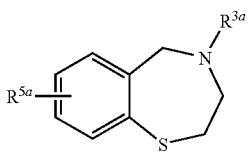

or with formaldehyde or a multimer thereof and a base to form an [N-hydroxymethyl-2-(acylaminoethyl)thio]benzene of formula

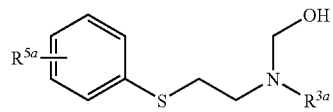

The [N-hydroxymethyl-2-(acylaminoethyl)thio]benzene can be further reacted with an acid to provide a protected benzothiazepine of formula

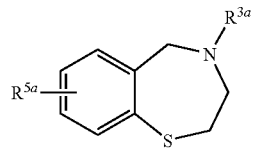

The $R^{3a}$ substituent is $(C_1-C_{10})$acyl of formula $-C(=O)-R^{18}$ or a nitrogen protecting group, the substituent $R^{5a}$ is H, $(C_1-C_4)$hydrocarbon, halogen, $-OR^6$, $-SR^6$, $-NO_2$, $-CN$, $-(C_1-C_4)$haloalkyl or $-O-(C_1-C_4)$haloalkyl, the substituent $R^6$ is H or $(C_1-C_6)$hydrocarbon; and the substitutent $R^{18}$ is H, $(C_1-C_6)$alkyl, $(C_1-C_4)$alkoxy, allyloxy, benzyloxy, substituted benzyloxy, fluorenylmethoxy or adamantyloxy.

Further cleaving results in the compound of formula

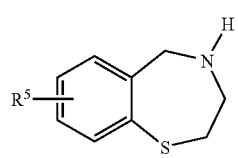

The compound can be further acylated with $R^3X$ to obtain a compound of formula

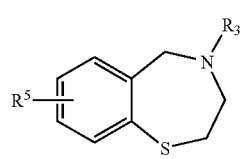

The $R^3$ substituent is $(C_1-C_{10})$acyl, $P(O)R^8R^9$, $C(=O)-R^{10}$, $C(=S)-R^{11}$, $S(=O)_2R^{12}$, $(CH_2)_mR^{13}$, a nitrogen protecting group, OH, $(C_1-C_6)$alkyl, cycloalkyl, aryl, heterocyclyl, heteroaryl, $(C_1-C_6)$alkyl-aryl, $(C_1-C_6)$alkyl-cycloalkyl, $(C_1-C_6)$alkyl-heterocyclyl or $(C_1-C_6)$alkyl-heteroaryl, each of the aryl, cycloalkyl, heterocyclyl and heteroaryl optionally substituted with one to three substituents independently selected from the group consisting of halogen, alkyl, alkoxyl, nitro, cyano and haloalkyl; $R^{10}$ and $R^{11}$ are each independently H, $-OR^{14}$, $-NR^{6a}R^{6b}$, $NHNHR^{15}$, NHOH, $CONH_2NHR^{15}$, $CO_2R^{15}$, $CONR^{15}$, halogen, alkoxy, aryloxy, allyloxy, benzyloxy, substituted benzyloxy, fluoroenylmethoxy, adamantyloxy, $(C_1-C_{20})$hydrocarbon, $(C_1-C_6)$alkyl, cycloalkyl, aryl, heterocyclyl, heteroaryl, $(C_1-C_6)$alkyl-aryl, $(C_1-C_6)$alkyl-cycloalkyl, $(C_1-C_6)$alkyl-heterocyclyl or $(C_1-C_6)$alkyl-heteroaryl, each of the aryl, cycloalkyl, heterocyclyl and heteroaryl optionally substituted with one to three substituents independently selected from the group consisting of halogen, alkyl, alkoxyl, nitro, cyano and haloalkyl; $R^{13}$ is $NH_2$, OH, $-SO_2R^{16}$, $-NHSO_2R^{16}$, C(=O)R$^{17}$, NH(C=O)R$^{17}$, —O(C=O)R$^{17}$, or —P(O)R$^8$R$^9$; m is an integer from 1-10; R$^{6a}$, R$^{6b}$, R$^{12}$, R$^{14}$, R$^{15}$, R$^{16}$ and R$^{17}$ are each independently at each of their occurrences H, —OR$^{15}$, —NR$^{15}$R$^{16}$, NHNHR$^6$, NHOH, (C$_1$-C$_{20}$)hydrocarbon, (C$_1$-C$_6$)alkyl, cycloalkyl, aryl, heterocyclyl, heteroaryl, (C$_1$-C$_6$)alkyl-aryl, (C$_1$-C$_6$)alkyl-cycloalkyl, (C$_1$-C$_6$)alkyl-heterocyclyl or (C$_1$-C$_6$)alkyl-heteroaryl, each of the aryl, cycloalkyl, heterocyclyl and heteroaryl optionally substituted with one to three substituents independently selected from the group consisting of halogen, alkyl, alkoxyl, nitro, cyano and haloalkyl, or R$^{6a}$ and R$^{6b}$, together with the nitrogen to which they are attached, represent a 5, 6, or 7-membered ring nitrogen-containing heterocycle; and X is halogen, (C$_1$-C$_{10}$)acyloxy, or an activated ester residue.

In another embodiment, further conversion of a compound of formula

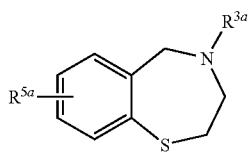

to a compound of formula

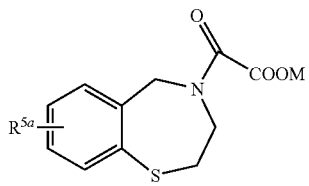

where M is H, ammonium, an alkali metal or an alkaline earth metal is accomplished by cleaving the R$^{3a}$ group to provide a 2,3,4,5-tetrahydrobenzo[f][1,4]thiazepine, acylating the 2,3,4,5-tetrahydrobenzo[f][1,4]thiazepine with an oxalate ester, and hydrolyzing the ester.

The hydrolysis step comprises treating the ester with a base or an acid and, optionally, when M is H, acidifying. The resulting product is optionally converted wherein M is H into a salt thereof. M could be a cation such as Na$^+$, Ca$^{++}$, Mg$^{++}$ or ammonium.

The [2-(acylaminoethyl)thio]arene compound used in the one step and the two steps ring closure may be obtained by reacting a compound of formula

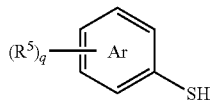

with a compound of formula

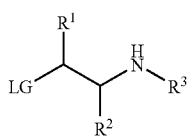

to provide a compound of formula

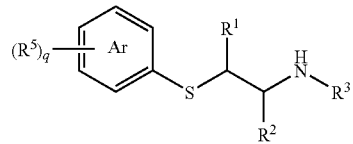

optionally in the presence of a base. LG is a leaving group for nucleophilic displacement by thio. Leaving groups for displacement by thiol are known in the art. They include halogens and sulfonates. Examples include chloro, iodo, bromo, methanesulfonate, toluenesulfonate, benzesulfonate, trifluoromethanesulfonate, nitrophenylsulfonate and bromophenylsulfonate.

In another embodiment, the [2-(acylaminoethyl)thio]arene compound may be obtained by reacting a compound of formula

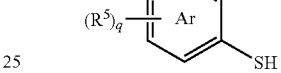

with a compound of formula

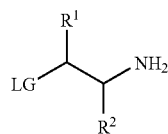

to provide a compound of formula

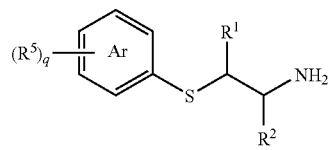

optionally in the presence of a base. The acyl substituent R$^3$ may be added in a second step reaction by a compound of formula R$^3$X, optionally in the presence of a base. LG is a leaving group for nucleophilic displacement by thiol and X is a leaving group for nucleophilic displacement by an amine. R$^3$X may thus be an acid chloride, an acid anhydride, an activated ester, a chloroformate, a sulfonyl chloride or a carbamic chloride. "Activated ester" is a term well known in the art, particularly the art of peptide synthesis, to denote esters that are capable of undergoing a substitution reaction with amines to form amides. The term includes esters "activated" by neighboring electron-withdrawing substituents. Examples include esters of phenols, particularly electronegatively substituted phenol esters such as pentafluorophenol esters; O-esters of isourea, such as arise from interaction with carbodiimides; O-esters of N-hydroxyamides and N-hydroxy heterocycles. Specific examples include S-t-butyl esters, S-phenyl esters, S-2-pyridyl esters, N-hydroxypiperidine esters, N-hydroxysuccinimide esters, N-hydroxyphthalimide esters and N-hydroxybenzotriazole esters.

In another embodiment, the invention comprises a process for 2,3,4,5-tetrahydro[1,4]thiazepine by cleaving the R$^3$ group to make a compound of formula

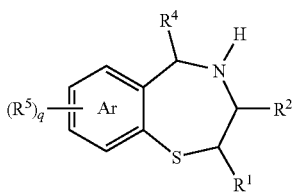

followed by a reaction with a compound of formula $R^3X$ optionally in the presence of a base; wherein X is a leaving group for nucleophilic displacement by an amine. The $R^3X$ is chosen from an acid chloride, an acid anhydride, an activated ester, a chloroformate and a carbamic chloride.

In one particular embodiment, the compound of formula

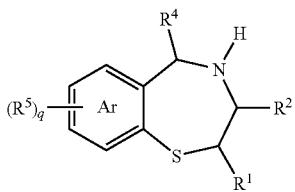

is reacted with a compound of formula $X-CH_2-COOR'$ wherein X is a halogen and R' is an alkyl to form an ester compound of formula:

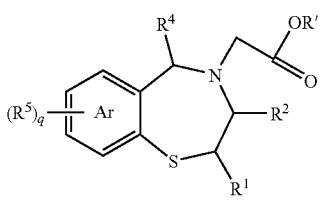

Followed by hydrolysis of the ester to form a compound of formula:

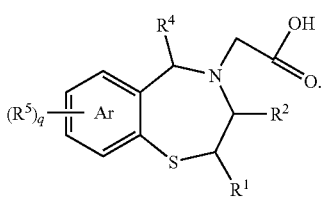

In one particular embodiment, the present invention provides methods for preparing a compound of formula

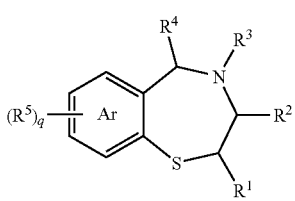

wherein Ar, $R^1$, $R^2$, $R^4$, $R^5$ and q are as defined above, and $R^3$ is $-C(=O)-R^{20}$ wherein $R^{20}$ is $N(R^{19})_2$, wherein each $R^{19}$ is independently chosen from hydrogen, alkyl, aryl, heterocyclyl, heteroaryl, alkylaryl, alkylheterocyclyl, or alkylheteroaryl; or taken together, $N(R^{19})_2$ represents a 5, 6, or 7-membered ring nitrogen-containing heterocycle. The 5, 6, or 7-membered ring nitrogen-containing heterocycle may be, for example, pyrrolidine, piperidine, morpholine, 4-CBZpiperazine or azepan. In accordance with this embodiment, the method comprises reacting a compound of formula

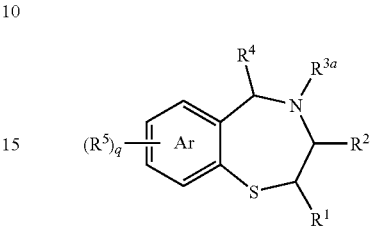

wherein Ar, $R^1$, $R^2$, $R^4$, $R^5$ and q are as defined above, and $R^{3a}$ is $-C(=O)-R^{21}$ wherein $R^{21}$ is $(C_1-C_4)$alkoxy, allyloxy, benzyloxy, substituted benzyloxy, fluorenylmethoxy or adamantyloxy, with an amine of formula $HN(R^{19})_2$ wherein each $R^{19}$ is independently as defined above, to form a compound of formula

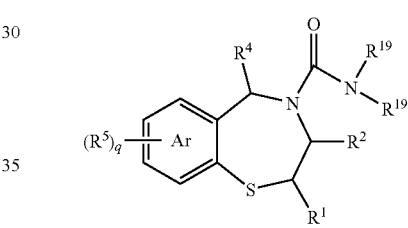

This embodiment has the advantages of simple and high yield synthesis of carbamates via the methods of the present invention, and further conversion of the carbamates to urea derivatives in a simple and efficient process that provides high quality product in high yields.

It is apparent to a person of skill in the art that the compounds of formula

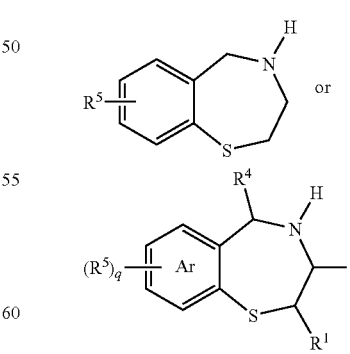

can be used as a starting material to prepare a variety of 1,4-benzothiazepine compounds, such as those described in U.S. patent application Ser. No. 11/506,285 (US 2007/0173482), Ser. No. 11/212,413 (US 2007/0049572), Ser. No.

11/212,309 (US 2006/0194767) and Ser. No. 10/809,089 (US 2005/0215540), the contents of which are incorporated by reference in their entirety.

EXAMPLES

Exemplary processes that fall within the scope of the invention are set forth below.

Example 1

Synthesis of 2-(7-methoxy-2,3-dihydrobenzo[f][1,4]thiazepin-4(5H)-yl)-2-oxoacetic acid (6) (Scheme 2)

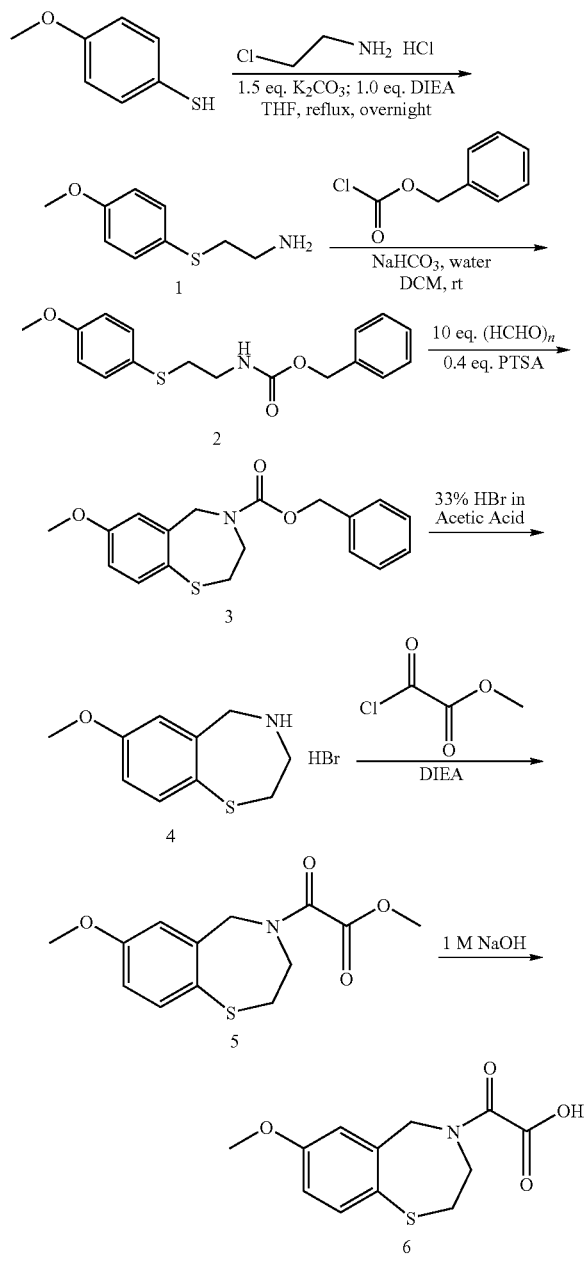

2-(4-Methoxyphenylthio)ethanamine (1)

4-Methoxythiophenol (50 g, 0.357 mol), 2-chloroethylamine monohydrochloride (39.8 g, 0.343 mol.), $K_2CO_3$ (78.8 g, 0.57 mol) and diisopropyl ethylamine (32 mL, 0.178 mol) were mixed in 200 mL of THF. The mixture was degassed for 5 min. under reduced pressure and refluxed under argon overnight. The solvent was removed and water (300 mL) was added to the flask. The mixture was extracted with dichloromethane (3×200 mL). The organics were collected, dichloromethane was removed and 50 mL conc. HCl was added, followed by 200 mL of water. The solution was extracted with 1:1 EtOAc/hexane (3×200 mL). The aqueous layer was adjusted to pH 10 with 2 M NaOH, and was extracted with dichloromethane (3×200 mL). The combined organic solution was dried over anhydrous sodium sulfate. Removal of solvent provided 61 g of the target compound as a colorless liquid, with a yield of 97%.

$^1$H-NMR (300 MHz, $CDCl_3$): 7.35 (d, J=8.7 Hz, 2H), 6.81 (d, J=8.7 Hz, 2H), 3.77 (s, 3H), 2.88-2.80 (m, 4H), 1.44 (s, 2H).

Benzyl 2-(4-methoxyphenylthio)ethylcarbamate (2)

First Method

To a the flask containing compound 1 (8.0 g, 43.7 mmol), sodium bicarbonate (12.1 g, 144 mmol), water (100 mL) and dichloromethane (200 mL) was added benzyl chloroformate (8.2 g, 48.1 mmol, diluted in 100 mL of dichloromethane) dropwise at 0° C. After the addition, the mixture was stirred at r.t. for 5 hr. The organic layer was collected and aqueous solution was extracted with 100 mL of dichloromethane. The combined organic solution was dried over sodium sulfate. The solvent was removed and the resulting solid was triturated with 200 mL of THF/hexane (1:10). The solid was collected and dried leaving the target product (12.9 g) in the yield of 93%.

Alternative Method

To the solution of compound 1 (10 g, 54.6 mmol) and triethylamine (15 mL, 106 mmol) in 200 mL of dichloromethane was added benzyl chloroformate (7.24 mL, 51.5 mmol, diluted in 100 mL of dichloromethane) dropwise at 0° C. After the addition, the solution was stirred at r.t. for one hour. The solid was removed by filtration. The solution was extracted with 100 mL of 0.1 M HCl and 100 mL of sat. sodium carbonate, and dried over anhydrous sodium sulfate. Removal of solvent provided a white solid that was stirred in 200 mL of THF/hexane (1:20) for three hours. The solid was collected by filtration to give 14.2 g of the target compound in 87% yield.

$^1$H-NMR (300 MHz, $CDCl_3$): 7.35 (m, 7H), 6.83 (d, J=8.7 Hz, 2H), 5.07 (m, 3H), 3.77 (s, 3H), 3.10 (q, J=6.3 Hz, 2H), 2.92 (t, J=6.3 Hz, 2H).

Benzyl 7-methoxy-2,3-dihydrobenzo[f][1,4]thiazepine-4(5H)-carboxylate (3)

A mixture of compound 2 (7.3 g, 23 mmol), paraformaldehyde (6.9 g 0.23 mol) and p-toluenesulfonic acid (1.45 g, 7.6 mmol) in 250 mL of toluene was stirred at 70° C. overnight. After cooling to r.t., the solid was filtered off. The solution was extracted with sat. sodium carbonate (100 mL), and the organic layer was dried over anhydrous sodium sulfate. The target product (7.4 g) was obtained as a liquid after removal of the solvent in 97% yield.

$^1$H-NMR (300 MHz, CDCl$_3$): 7.44 (d, J=8.1 Hz, 0.77H), 7.32 (m, 5.60H), 7.07 (d, J=2.7 Hz, 0.33H), 6.68 (m, 1.30H), 5.04 (s, 2H), 4.59 (ss, 2H), 3.96 (br, 1.80), 3.80 (ss, 1.23H), 3.55 (s, 1.97H), 2.76 (m, 2H).

7-Methoxy-2,3,4,5-tetrahydrobenzo[f][1,4]thiazepine hydrobromide (4 HBr salt)

First Method

A solution of HBr (33% in acetic acid, 10 mL) was added to the compound 3 (4.2 g, 12.8 mmol). After the addition, carbon dioxide began to develop and a white solid formed. The mixture was let stand at r.t. for another 2 hours. Diethyl ether (150 mL) was added to the mixture, and it was stirred for 30 min. The solid was collected by filtration and washed with diethyl ether. The solid was dried under vacuum to give the 3.40 g of the target compound with the yield of 91.8%.

$^1$H-NMR (300 MHz, DMSO-d$_6$): 9.02 (br, 2H), 7.52 (d, J=8.1 Hz, 1H), 7.27 (d, J=3.3 Hz, 1H), 6.92 (dd, J=8.4, 2.7 Hz, 1H), 4.41 (s, 2H), 3.77 (s, 3H), 3.53 (m, 2H), 2.96 (m, 2H).

Alternative Method (Free Base 4a)

Compound 3 (10 g, 30 mmol) was mixed with 50 mL of conc. HCl, 50 mL of water and 30 mL of dioxane. The mixture was stirred at 100° C. overnight. After cooling to r.t., most of the solvent and HCl was removed under reduced pressure. Water (100 mL) was added to the solution and the solid was filtered off. The aqueous solution was extracted with EtOAc/hexane (1:1, 3×100 mL) and basified by adding 15 g of NaOH. The mixture was extracted with dichloromethane (3×150 mL). The combined solution was dried over anhydrous sodium sulfate. Removal of solvent provided a liquid that solidified after standing at rt. leaving 6.2 g of target compound.

$^1$H-NMR (300 MHz, CDCl$_3$): 7.42 (d, J=8.1 Hz, 1H), 6.78 (d, J=2.7 Hz, H), 6.68 (dd, J=2.7, 8.1 Hz, 1H), 4.08 (s, 2H), 3.96 (br, 1.80), 3.76 (s, 3H), 3.38 (m, 2H), 2.68 (m, 2H).

Methyl 2-(7-methoxy-2,3-dihydrobenzo[f][1,4]thiazepin-4(5H)-yl)-2-oxoacetate (5)

To a solution of compound 4 (580 mg, 2.97 mmol) and diisopropyl ethylamine (1.0 mL, 5.5 mmol) in 20 mL of dichloromethane was added methyl chlorooxoacetate (301 μl, 3.27 mmol). The solution was stirred at r.t. for 4 hr. It was diluted with 40 mL of dichloromethane and extracted with 1M HCl (2×30 mL). The organic layer was dried over sodium sulfate. Removal of solvent provided the target compound (740 mg) with the yield of 89%.

$^1$H-NMR (300 MHz, CDCl$_3$): 7.46 (d, J=8.4 Hz, 1H), 7.09 (d, J=2.7 Hz, 1H), 6.73 (m, 1H), 4.76 (br, 2H), 4.06 (m, 0.6H), 3.87 (m, 7.4H), 2.81 (m, 2H).

2-(7-Methoxy-2,3-dihydrobenzo[f][1,4]thiazepin-4 (5H)-yl)-2-oxoacetic acid (6)

Compound 5 (740 mg) was dissolved in 30 mL of a mixture of THF, methanol and 1 M NaOH (1:1:1). The solution was stirred at r.t. for 6 hr and acidified with 1 N HCl. The organic solvent was removed and the resulting solid was collected and washed with water. The solid was dried under vacuum to give 600 mg solid with the yield of 85%.

$^1$H-NMR (300 MHz, DMSO-d$_6$): 7.43 (m, 2H), 7.00 (d, J=2.7 Hz, 1H), 6.79 (m, 1H), 4.66 (ss, 2H), 3.98-3.82 (m, 2H), 3.73 (ss, 3H), 2.83 (m, 2H).

Example 2

Synthesis of Compound 38 (e.g., 7-methoxy-2,3-dihydrobenzo[f][1,4]thiazepin-4(5H)-yl)(piperazin-1-yl)methanone (ARM064)) (Scheme 3)

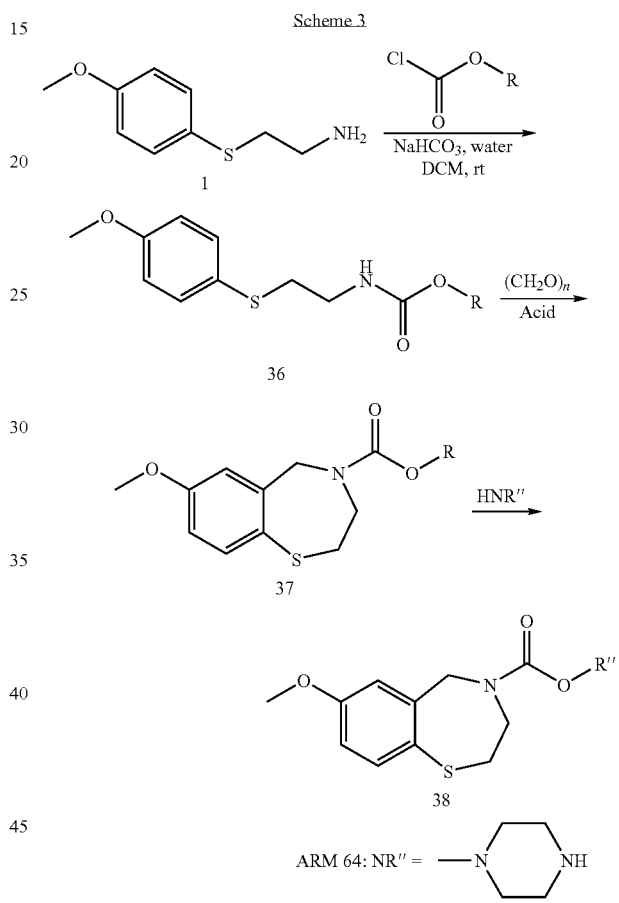

Compound 1 reacts with ClC(=O)OR to form compound 36, wherein R is phenyl, 4-NO$_2$-phenyl, methyl, ethyl, benzyl, allyl, CH$_2$CCl$_3$, CH$_2$CF$_3$ or other group which, together with the oxygen to which they are attached, could serve as a leaving group when reacted with an amine. Compound 36 reacts with (CH$_2$O)$_m$, in an acid to form compound 37. Heating the mixture of compound 37 and an amine (HNR") in the presence of a base or a catalyst such as Al(CH$_3$)$_3$ (Janda, K D. et. al. *Tetrahedron* 2004, 60, 3439), or γ-Al$_2$O$_3$ (Vauthey, I. et. al. *Tetrahedron Lett.* 2000, 41, 6347), affords compound 38. Alternatively, the reaction between compound 37 and the amine (HNR") can be catalyzed by using metal catalyst such as Zr(Ot-Bu)$_4$ (Porco, J A. et. al. *Organic Lett.* 2007, 1517). For the preparation of ARM064, HNR" is piperazine or a Boc-protected piperazine. When Boc-protected piperazine is used, the Boc group can be removed in acid such as TFA. The resulting compound 38 is ARM064. Yield: 85%-95%.

Example 3

Synthesis of Compound 38 (e.g., 7-methoxy-2,3-dihydrobenzo[f][1,4]thiazepin-4(5H)-yl)(piperazin-1-yl)methanone (ARM064)) (Scheme 4)

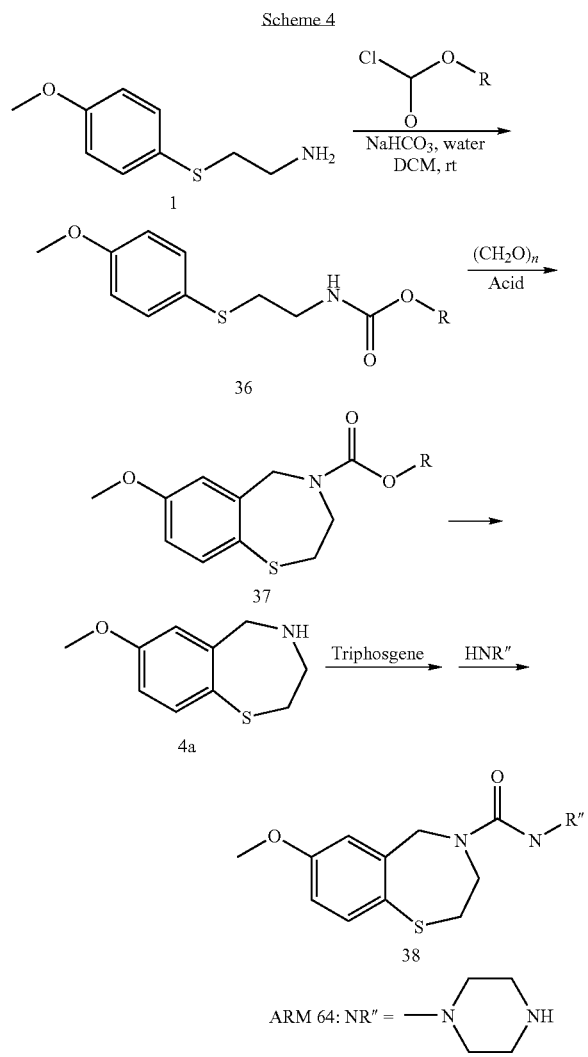

Example 4

Synthesis of methyl 7-methoxy-2,3-dihydrobenzo[f][1,4]thiazepine-4(5H)-carboxylate (8) (Scheme 5)

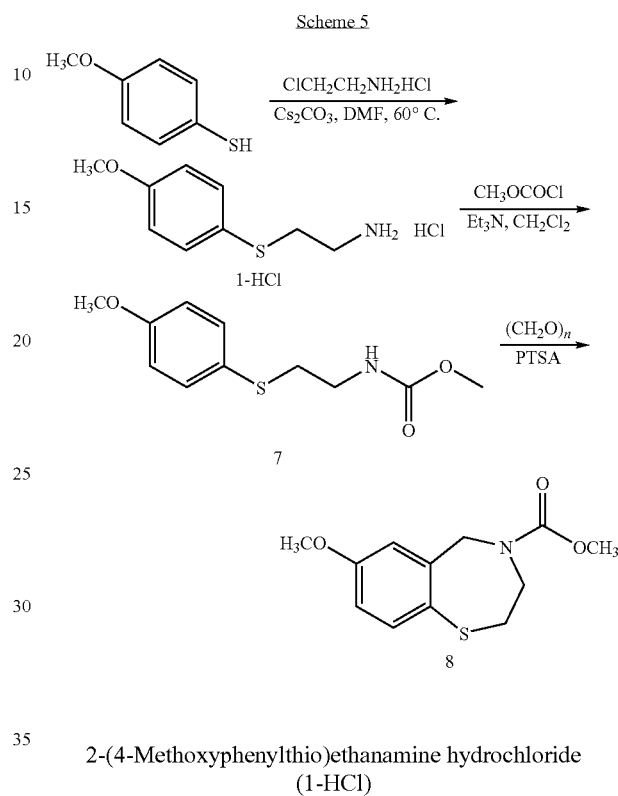

2-(4-Methoxyphenylthio)ethanamine hydrochloride (1-HCl)

A mixture of 4-methoxybenzenethiol (25 g), 2-chloroethylamine HCl (1.1 eq.) and $Cs_2CO_3$ (2.4 eq.) in DMF (200 mL) was stirred at 60° C. for 2 days. The solvents were removed by evaporation under reduced pressure and the crude product was dissolved in 300 mL of EtOAc. The organic phase was washed with $H_2O$ (2×50 mL) and concentrated under reduced pressure. The residue was dissolved in 200 mL 1N HCl and washed with EtOAc (2×50 ml). Evaporation of the aqueous phase gave the desired product as HCl salt and white solid. Yield: 34.8 g, 91%. (The free amine can be obtained by treatment of the salt with 1N NaOH).

Methyl 2-(4-methoxyphenylthio)ethylcarbamate (7)

To a solution of compound 1-HCl (0.466 g) in $CH_2Cl_2$ (20 mL) cooled to ~0° C. was added methyl chloroformate (1.1 eq.) and triethylamine (2.5 eq.). The reaction mixture was stirred for 2 hours at 0° C. and washed with 1N HCl, and sat. $NaHCO_3$. The solvents were removed by evaporation under reduced pressure to give product 7 as white solid with a yield of 480 mg, 98%.

$^1$N-NMR (300 MHz, $CDCl_3$): δ:7.4 (d, 2H), 6.8 (d, 2H), 5.1 (broad, 1H), 3.8 (s, 3H), 3.65 (s, 3H), 3.30 (t, 2H), 2.95 (t, 2H).

Methyl 7-methoxy-2,3-dihydrobenzo[f][1,4]thiazepine-4(5H)-carboxylate (8)

A mixture of compound 7 (95 mg), paraformaldehyde (95 mg, excess), p-toluenesulfonic acid (30 mg) in benzene (4

Compound 1 reacts with ClC(=O)OR to form compound 36, wherein R is phenyl, 4-$NO_2$-phenyl, methyl, ethyl, benzyl, allyl, $CH_2CCl_3$, $CH_2CF_3$ or other group which could serve as a leaving group when reacted with an amine. Compound 36 reacts with $(CH_2O)_n$, in an acid to form compound 37. The carbamate group is then removed to afford the free amine, compound 4a. When R is benzyl, carbamate 37 can be converted into compound 4 or its free base compound 4a, as described in Example 1 with respect to conversion of compound 3 to compounds 4 and 4a. Compound 4a (or 4) is reacted with triphosgene followed by an amine (HNR") optionally in the presence of a base. For the preparation of ARM064, HNR" is preferably a Boc-protected piperazine. When Boc-protected piperazine is used, the Boc group can be removed in acid such as TFA. The resulting compound 38 is ARM064.

mL) was stirred at 60° C. overnight. Analysis by TLC showed a new spot and the complete disappearance of the starting material. Filtration, followed by concentration and chromatography on $SiO_2$ gave 92 mg of pure product 8. Yield: 95%.

$^1$H-NMR (300 MHz, $CDCl_3$): δ:7.40 (d, 0.6H), δ:7.38 (d, 0.4H), 6.98 (s, 0.4H), 6.80 (s, 0.6H), 6.61 (d, 1H), 4.35 (s, 0.4×2H), 4.30 (s, 0.6×2H), 3.89 (s, broad, 2H), 3.70 (s, 3H), 3.60 (s, 0.6×3H), 2.90 (m, 2H).

Example 5

Synthesis of methyl 7-methoxy-2,3-dihydrobenzo[f][1,4]thiazepine-4(5H)-carboxylate (8) (Scheme 6)

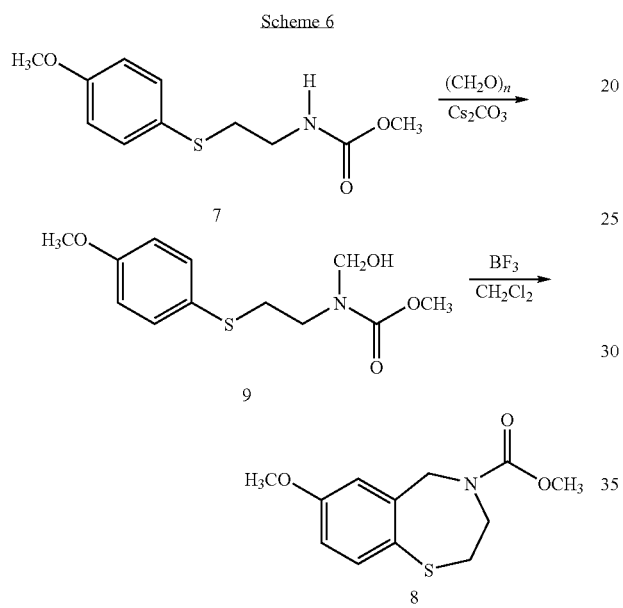

Methyl hydroxymethyl(2-(4-methoxyphenylthio)ethyl)carbamate (9)

A mixture of compound 7 (2.0 g), paraformaldehyde (1.5 g), $Cs_2CO_3$ (1.2 eq.) in THF (50 mL) was stirred at 70° C. for 3 hours. Filtration and concentration of the solvent gave the title product 9 as pure white solid. Yield: 2.2 g, 98%.

$^1$H-NMR (300 MHz, $CDCl_3$): δ:7.4 (d, 2H), 6.89 (d, 2H), 4.7 (broad, 2H), 3.75 (s, 3H), 3.65 (s, 3H), 3.40 (t, 2H), 2.95 (t, 2H).

Methyl 7-methoxy-2,3-dihydrobenzo[f][1,4]thiazepine-4(5H)-carboxylate (8)

A solution of compound 9 (20.0 mg) in 10 mL $CH_2Cl_2$ was treated with 1.1 eq. of $BF_3$—$OEt_2$ under Ar. The mixture was stirred overnight and washed with 1N HCl and sat. $NaHCO_3$ Removal of the solvent gave the crude product and TLC analysis showed one major spot. The crude product was further purified on $SiO_2$ column to provide the title compound (16 mg). The structure was confirmed by NMR and TLC comparison with authentic sample prepared by the reaction of 7-MeO-2,3,4,5-tetrahydro-1,4-benzothiazepine with methyl chloroformate.

$^1$H-NMR ($CDCl_3$): δ:7.40 (d, 0.6H), δ:7.38 (d, 0.4H), 6.98 (s, 0.4H), 6.80 (s, 0.6H), 6.61 (d, 1H), 4.35 (s, 0.4×2H), 4.30 (s, 0.6×2H), 3.89 (s, broad, 2H), 3.70 (s, 3H), 3.60 (s, 0.6×3H), 2.90 (m, 2H).

Example 6

Synthesis of 1-(7-methoxy-2,3-dihydrobenzo[f][1,4]thiazepin-4(5H)-yl)ethanone (11) (Scheme 7)

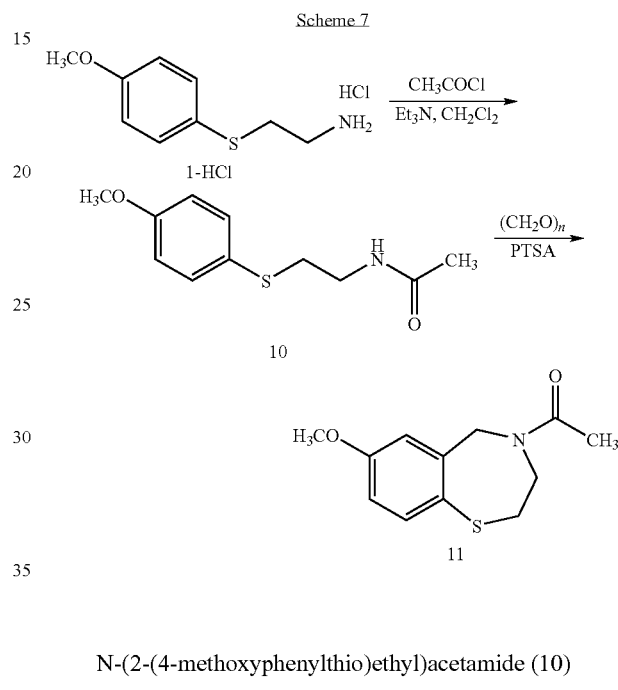

N-(2-(4-methoxyphenylthio)ethyl)acetamide (10)

To a solution of compound 1-HCl (0.44 g) in $CH_2Cl_2$ (15 mL) cooled to ~0° C. was added acetyl chloride (1.0 mL) and triethylamine (1.0 mL). The reaction mixture was stirred for 1 hour at 0° C. and washed with 1N HCl, sat. $NaHCO_3$. The solvents were removed by evaporation under reduced pressure to give product 10 as solid (pure by TLC and NMR). Yield: 0.5 g.

$^1$H-NMR (300 MHz, $CDCl_3$): δ:7.4 (d, 2H), 6.8 (d, 2H), 5.90 (s, broad, 1H), 3.8 (s, 3H), 3.40 (t, 2H), 2.95 (t, 2H), 2.1 (s, 3H).

1-(7-Methoxy-2,3-dihydrobenzo[f][1,4]thiazepin-4(5H)-yl)ethanone (11)

A mixture of compound 11 (70 mg), paraformaldehyde (70 mg), p-toluenesulfonic acid (40 mg) in benzene (4 mL) was stirred at 70° C. overnight. Filtration, followed by washing with sat. $NaHCO_3$ solution gave crude product, which was purified by chromatography on $SiO_2$ gave the target compound (11) in 91% yield.

$^1$H-NMR (300 MHz, $CDCl_3$): δ:7.50 (d, 0.6H), δ:7.38 (d, 0.4H), 7.10 (s, 0.4H), 6.80 (s, 0.6H), 6.70 (m, 1H), 4.70 (s, 0.4×2H), 4.60 (s, 0.6×2H), 4.10 (s, broad, 0.6×2H), 3.90 (s, broad, 0.4×2H), 3.80 (s, 0.4×3H), 3.79 (s, 0.6×3H), 2.90 (m, 2H), 2.2 (s, 0.4×3H), 2.06 (s, 0.6×3H).

Example 7

Synthesis of 2,2,2-trifluoro-1-(7-methoxy-2,3-dihydrobenzo[f][1,4]thiazepin-4(5H)-yl)ethanone (13) (Scheme 8)

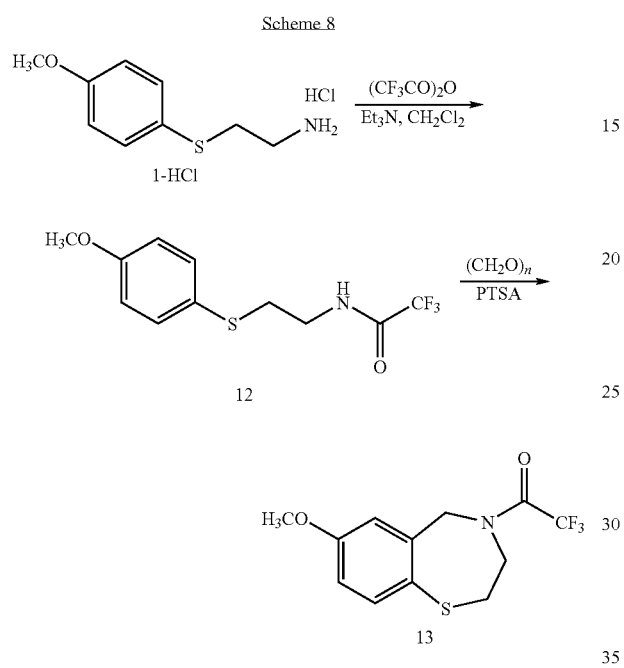

2,2,2-Trifluoro-N-(2-(4-methoxyphenylthio)ethyl)acetamide (12)

To a solution of compound 1 (as hydrochloride, 1.8 g) in CH$_2$Cl$_2$ (20 mL) cooled to 4° C. and was added trifluoroacetic anhydride (1.1 eq.) and triethylamine (1.5 eq.). The reaction mixture was stirred at r. t. overnight and washed with 1N HCl and sat. NaHCO$_3$. The solvents were removed by evaporation under reduced pressure to give product 12 as solid (pure by TLC and NMR). Yield: 2.5 g.

$^1$H-NMR (300 MHz, CDCl$_3$): δ:7.4 (d, 2H), 6.8 (d, 2H), 6.6 (s, broad, 1H), 3.8 (s, 3H), 3.40 (t, 2H), 2.95 (t, 2H).

2,2,2-Trifluoro-1-(7-methoxy-2,3-dihydrobenzo[f][1,4]thiazepin-4(5H)-yl)ethanone (13)

A mixture of compound 12 (100 mg), paraformaldehyde (100 mg), p-toluenesulfonic acid (60 mg) in toluene (10 mL) was stirred at 80° C. overnight. Filtration, followed by washing with sat. NaHCO3 solution gave crude product 13 in an estimated yield of ~70% by TLC and NMR.

$^1$H-NMR (300 MHz, CDCl$_3$): δ:7.45 (d, 1H), 7.05 (s, 1H), 6.7 (d, 1H), 4.6 (m, 2H), 4.0 (m, 2H), 3.8 (s, 3H), 2.9 (m, 2H).

Example 8

Synthesis of 7-methoxy-2,3-dihydrobenzo[f][1,4]thiazepine-4(5H)-carbaldehyde (15) (Scheme 9)

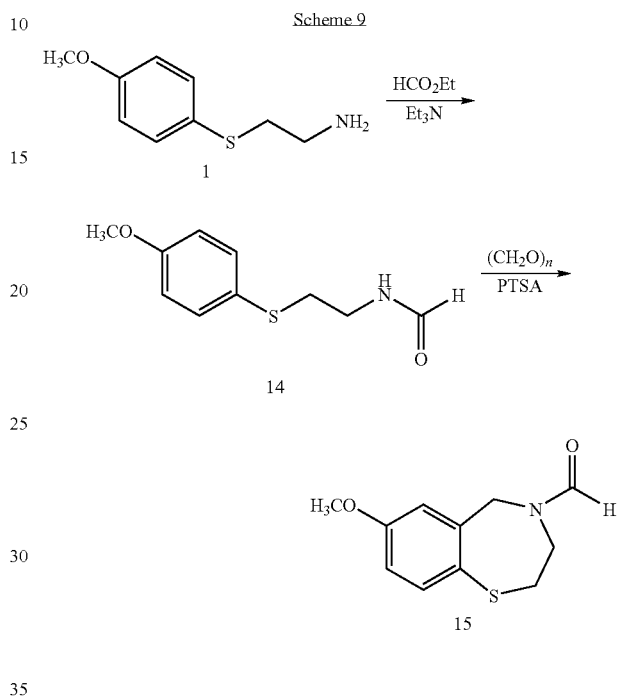

N-(2-(4-Methoxyphenylthio)ethyl)formamide (14)

A solution of compound 1 (550 mg) and Et$_3$N (1 mL) in HCO$_2$Et (20 mL) was refluxed for 12 h. The mixture was cooled down and washed with 1 N HCl and sat. NaHCO$_3$. The solvents were removed by evaporation under reduced pressure to give product 14 as solid: 606 mg. The crude product appeared to be pure by TLC and NMR and used for the next step reaction without further purification.

$^1$H-NMR (300 MHz, CDCl$_3$): 8.15 (s, 1H), 7.4 (d, 2H), 6.8 (d, 2H), 6.2 (s, broad, 1H), 3.8 (s, 3H), 3.40 (t, 2H), 2.95 (t, 2H).

7-Methoxy-2,3-dihydrobenzo[f][1,4]thiazepine-4(5H)-carbaldehyde (15)

A mixture of compound 14 (100 mg), paraformaldehyde (100 mg), p-toluenesulfonic acid (60 mg) in benzene (5 mL) was stirred at 70-75° C. for 2 days. Filtration, washing with sat. NaHCO$_3$ and concentration gave crude product 15 in an estimated yield of ~70% by TLC and NMR.

$^1$H-NMR (CDCl$_3$): δ:8.2 (s, 1H), 7.50 (d, 1H), 7.10 (s, 1H), 6.80 (d, 1H), 4.80 (s, broad, 2H), 4.10 (s, broad, 2H), 3.80 (s, 3H), 2.90 (m, 2H).

Example 9

Synthesis of (7-methoxy-2,3-dihydrobenzo[f][1,4]thiazepin-4(5H)-yl)(morpholino)methanone (17) (Scheme 10)

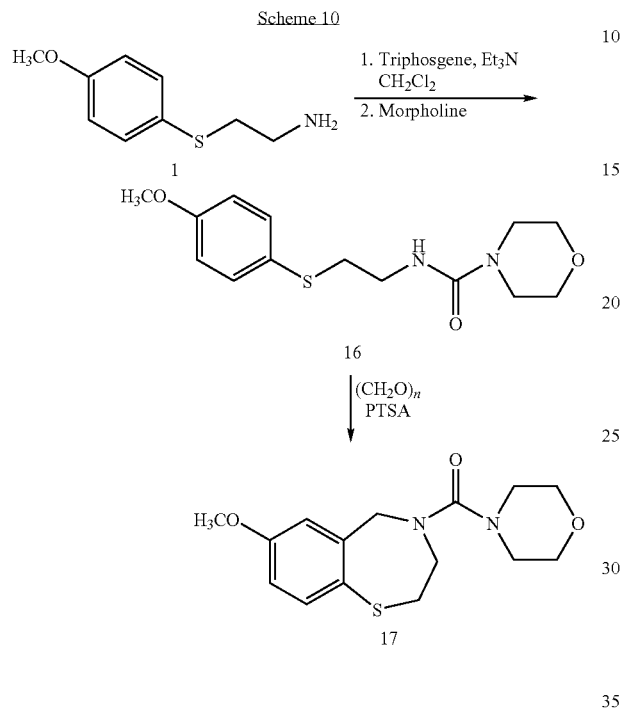

N-(2-(4-Methoxyphenylthio)ethyl)morpholine-4-carboxamide (16)

To a solution of compound 1 (400 mg) in CH$_2$Cl$_2$ (10 mL) was added triphosgene (1.0 eq.) and triethylamine (2.5 eq.) at 0° C. The reaction mixture was stirred for 2 h. at r. t and morpholine (3.0 eq.) was added. The reaction was stirred until it appeared by TLC to be completed (~4 h), and was washed with 1N HCl and sat NaHCO$_3$ (3×10 mL). The solvents were removed by evaporation under reduced pressure to give product 16 (520 mg). The crude product appeared to be pure by TLC and NMR and used for the next step reaction without further purification.

$^1$H-NMR (300 MHz, CDCl$_3$): δ:7.4 (d, 2H), 6.8 (d, 2H), 3.75 (s, 3H), 3.65 (m, 4H), 3.40 (t, 2H), 3.28 (m, 4H), 2.95 (t, 2H).

(7-Methoxy-2,3-dihydrobenzo[f][1,4]thiazepin-4(5H)-yl)(morpholino)methanone (17)

A mixture of compound 16 (100 mg), paraformaldehyde (110 mg), p-toluenesulfonic acid (60 mg) in benzene (5 mL) was stirred at 70-75° C. for 14 h. The reaction solution was filtrated, washed with sat. NaHCO$_3$ and concentrated to give crude title product 17 in an estimated yield of ~50% by TLC and NMR. Chromatography on SiO$_2$ (CH$_2$Cl$_2$/EtOAc 10:1) provided pure sample for confirmation of the structure.

$^1$H-NMR (300 MHz, CDCl$_3$): δ:7.4 (d, 1H), 6.95 (s, 1H), 6.7 (d, 1H), 4.5 (s, 2H), 3.80 (s, 3H), 3.79 (s, broad, 2H), 3.70 (m, 4H), 3.10 (m, 4H), 2.95 (t, 2H).

Example 10

Synthesis of Benzyl 4-(7-methoxy-2,3,4,5-tetrahydrobenzo[f][1,4]thiazepine-4-carbonyl)piperazine-1-carboxylate (19) (Scheme 11)

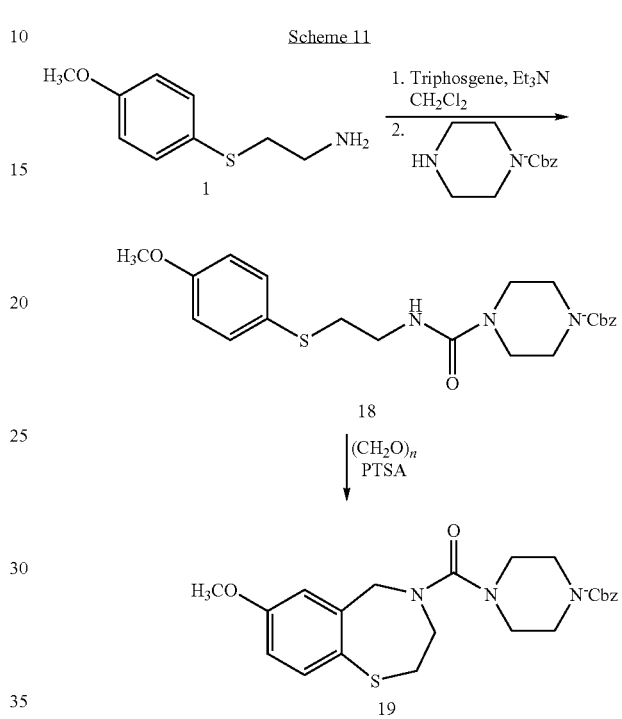

Benzyl 4-(2-(4-methoxyphenylthio)ethylcarbamoyl)piperazine-1-carboxylate (18)

To a solution of compound 1 (183 mg) in CH$_2$Cl$_2$ (10 mL) was added triphosgene (0.7 eq.) and triethylamine (1.0 eq.) at 0° C. The reaction mixture was stirred for 1 h. at r.t., and N-Cbz-piperidine (1.5 eq.) and Et$_3$N (0.5 mL) were added. The reaction mixture was stirred overnight and washed with 1N HCl and sat NaHCO$_3$ (3×5 mL). The solvents were removed by evaporation under reduced pressure to give the title product 18, which was purified by chromatography (SiO$_2$, CH$_2$Cl$_2$/EtOAc 10:1). Yield: 360 mg.

$^1$H-NMR (300 MHz, CDCl$_3$): δ:7.4 (d, 2H), 7.30 (s, 5H), 6.8 (d, 2H), 6.6 (s, broad, 1H), 5.15 (s, 2H), 3.75 (s, 3H), 3.50 (m, 4H), 3.40 (t, 2H), 3.30 (m, 4H), 2.95 (t, 2H).

Benzyl 4-(7-methoxy-2,3,4,5-tetrahydrobenzo[f][1,4]thiazepine-4-carbonyl)piperazine-1-carboxylate (19)

A mixture of compound 18 (30 mg), paraformaldehyde (100 mg), p-toluenesulfonic acid (30 mg) in benzene (5 mL) was stirred at 70-75° C. for 2 days. The reaction mixture was filtered, washed with sat. NaHCO$_3$ and concentrated to give crude product 19, which was purified by chromatography on SiO$_2$ (CH$_2$Cl$_2$/EtOAc 10:1). Yield: 21 mg, 69%.

$^1$H-NMR (300 MHz, CDCl$_3$): δ:7.4 (d, 1H), 7.35 (s, 5H), 6.85 (s, 1H), 6.70 (d, 1H), 5.15 (s, 2H), 4.5 (s, 2H), 3.80 (s, 3H), 3.75 (s, broad, 2H), 3.60 (m, 4H), 3.20 (m, 4H), 2.95 (t, 2H).

Example 11

Synthesis of benzyl 8-methoxy-2,3-dihydrobenzo[f][1,4]thiazepine-4(5H)-carboxylate (22) and benzyl 6-methoxy-2,3-dihydrobenzo[f][1,4]thiazepine-4(5H)-carboxylate (23) (Scheme 12)

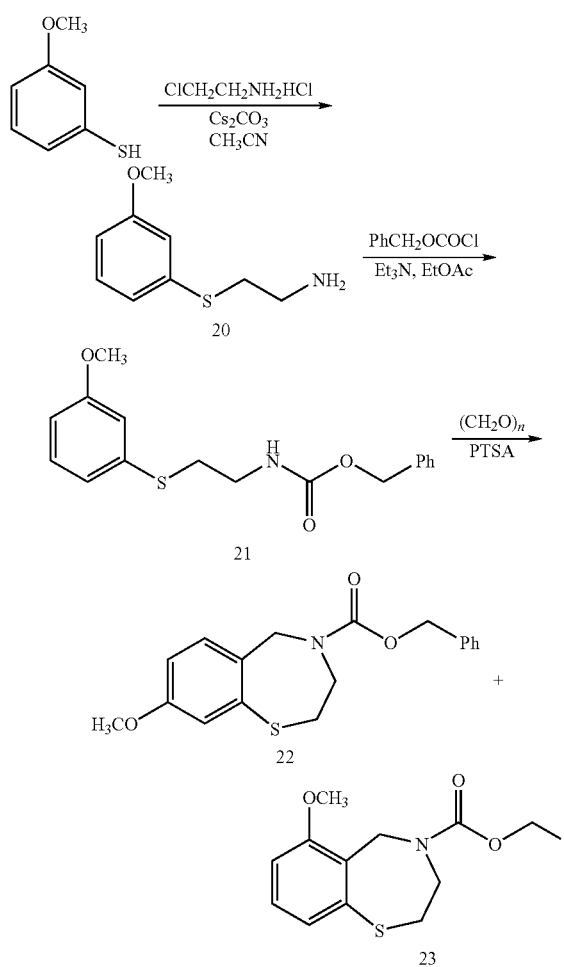

2-(3-Methoxyphenylthio)ethanamine (20)

A mixture of 3-methoxybenzenethiol (5 g), 2-chloroethylamine hydrochloride (1.1 eq.) and Cs$_2$CO$_3$ (2.2 eq.) in CH$_3$CN (60 mL) was stirred at 60° C. for 20 h. To the reaction mixture, EtOAc (100 mL) was added, and washed with H$_2$O (2×30 mL). The organic phase was concentrated under reduced pressure to give product 20 (Yield: 6.2 g, 95%), which appeared to be pure by TLC and NMR and was used for the next step reaction without further purification.

Benzyl 2-(3-methoxyphenylthio)ethylcarbamate (21)

To a solution of compound 20 (1.0 g) in EtOAc (50 mL) cooled to ~0° C. was added benzyl chloroformate (1.1 eq.) and triethylamine (1.2 eq.). The reaction mixture was stirred for 4 hours at r.t. and washed with 1N HCl, and sat. NaHCO$_3$ (2×10 mL). The solvents were removed by evaporation under reduced pressure to give crude title product. Purification by chromatography gave 21 as white solid. Yield: 1.61 g.

$^1$H-NMR (300 MHz, CDCl$_3$): δ:7.4 (s, 5H), 7.2 (m, 1H), 6.95 (d, 1H), 6.90 (s, 1H), 6.7 (d, 1H), 5.15 (s, broad, 2H), 3.8 (s, 3H), 3.40 (t, 2H), 2.95 (t, 2H).

Benzyl 8-methoxy-2,3-dihydrobenzo[f][1,4]thiazepine-4(5H)-carboxylate (22) and benzyl 6-methoxy-2,3-dihydrobenzo[f][1,4]thiazepine-4(5H)-carboxylate (23)

A mixture of compound 21, paraformaldehyde (100 mg), p-toluenesulfonic acid (50 mg) in benzene (5 mL) was stirred at 76° C. for 20 h. Filtration, followed by concentration and chromatography on SiO$_2$ gave a mixture of products 22 and 23 in a ratio of 50:1. Total yield: 83 mg.

$^1$H-NMR (CDCl$_3$): 7.80 (d, 0.5×1H), 7.45-7.2 (m, 6H), 7.08 (m), 6.95 (s, 0.4×1H), 6.80 (d), 6.68 (d), 6.70 (d, 0.6×1H), 5.1 (s), 5.0 (s), 4.7 (s, broad), 4.6 (s), 4.05 (s, broad, 2H), 3.82 (s, 0.6×3H), 3.80 (s, 0.3×3H), 2.8 (m, 2H).

Example 12

Synthesis of benzyl 7-methyl-2,3-dihydrobenzo[f][1,4]thiazepine-4(5H)-carboxylate (26) (Scheme 13)

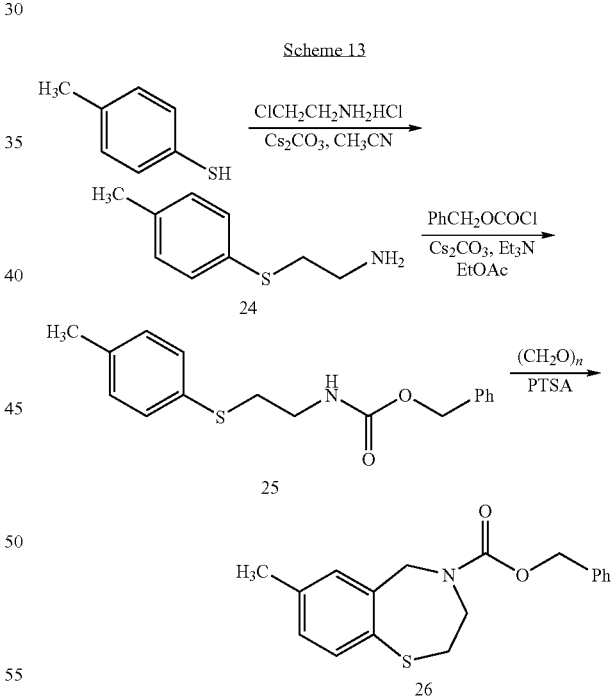

2-(p-Tolylthio)ethanamine (24)

A mixture of 4-methylbenzenethiol (1.24 g), 2-chloroethylamine HCl (2.3 g) and Cs$_2$CO$_3$ (5.3 g) in CH$_3$CN (30 mL) was stirred at 50° C. for 2 days. To the reaction mixture were added EtOAc (50 mL) and H$_2$O (30 mL). The organic phase was separated, washed with H$_2$O (2×30 mL) and concentrated under reduced pressure to give product 24. Yield: 1.67 g, 95%.

$^1$H-NMR (300 MHz, CDCl$_3$): δ:7.27 (d, 2H), 7.13 (d, 2H), 3.0 (t, 2H), 2.8 (t, 2H), 2.3 (s, 3H).

Benzyl 2-(p-tolylthio)ethylcarbamate (25)

To a solution of compound 24 (1.60 g) in EtOAc (100 mL) was added benzyl chloroformate (2.0 g, 1.2 eq.) and Cs$_2$CO$_3$ (3.2 g, 3 eq.). The reaction mixture was stirred at r.t. for 5 h. Triethylamine (2 mL) was added and the reaction was stirred for 3 h. After addition of H$_2$O (30 mL), the organic phase was separated and washed with 1N HCl (2×30 mL), and sat. NaHCO$_3$ (2×30 mL). The solvent was removed by evaporation under reduced pressure to give product 25 as white solid. Yield: 2.4 g, 79.7%.

$^1$H-NMR (300 MHz, CDCl$_3$): δ: 7.35 (m, 5H), 7.3 (d, 2H), 7.1 (d, 2H), 5.1 (s, broad, 2H), 3.4 (s, broad, 2H), 3.0 (t, 2H), 2.3 (s, 3H).

Benzyl 7-methyl-2,3-dihydrobenzo[f][1,4]thiazepine-4(5H)-carboxylate (26)

A mixture of compound 25(120 mg), paraformaldehyde (120 mg, excess), p-toluenesulfonic acid (40 mg) in toluene (10 mL) was stirred at 70° C. for 24 h. The reaction mixture was filtered and washed with sat. NaHCO$_3$ (2×5 mL). Removal of the solvent gave product 26 as a pure product by TLC and NMR. Yield: 110 mg, 89%.

$^1$H-NMR (300 MHz, CDCl$_3$): δ:7.40 (m, 7H), 6.95 (d, 1H), 5.1 (s, 2H), 4.5 (s, 2H), 4.0 (m, 2H), 2.8 (m, 2H), 2.1 (s, 3H).

Example 13

Synthesis of benzyl 7-(methylthio)-2,3-dihydrobenzo[f][1,4]thiazepine-4(5H)-carboxylate (28) (Scheme 14)

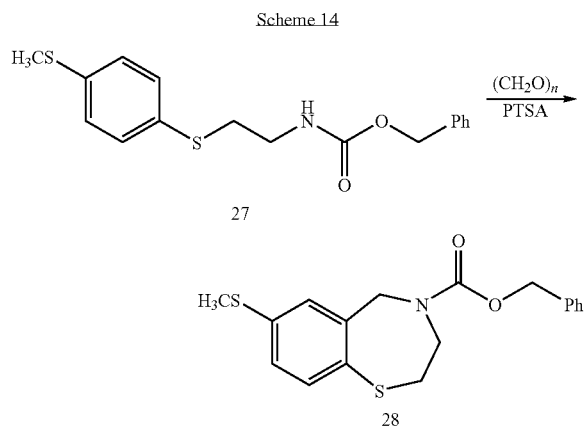

Benzyl 7-(methylthio)-2,3-dihydrobenzo[f][1,4]thiazepine-4(5H)-carboxylate (28)

A mixture of compound 27 (3 g), paraformaldehyde (3.5 g, excess), p-toluenesulfonic acid (1.5 g) in benzene (120 mL) was stirred at 80° C. for 14 h. The reaction mixture was filtered and washed with sat. NaHCO$_3$ (3×30 mL). Removal of the solvent gave compound 28 as white solid. Yield: 2.98 g, 90%.

$^1$H-NMR (300 MHz, CDCl$_3$): δ:7.40 (m, 6H), 7.0 (m, 2H), 5.1 (s, 2H), 4.5 (s, 2H), 4.0 (m, 2H), 2.8 (m, 2H), 2.2 (s, 3H).

Example 14

Synthesis of 7-(trifluoromethoxy)-2,3,4,5-tetrahydrobenzo[f][1,4]thiazepine hydrobromide (31) (Scheme 15)

Scheme 15

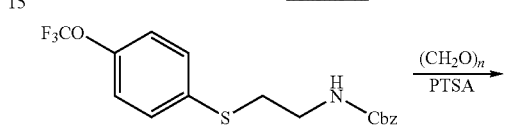

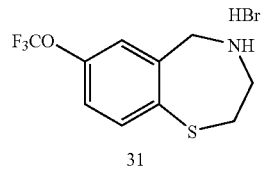

Benzyl 7-(trifluoromethoxy)-2,3-dihydrobenzo[f][1,4]thiazepine-4(5H)-carboxylate (30)

A mixture of benzyl 2-(4-(trifluoromethoxy)phenylthio)ethylcarbamate (29) (300 mg), paraformaldehyde (300 g), p-toluenesulfonic acid (100 g) in benzene (15 mL) was stirred at 80° C. for 3 days. The reaction mixture was filtered and washed with sat. NaHCO$_3$ (2×5 mL). Removal of the solvent gave 30 as white solid. The product was purified by chromatography on SiO$_2$ (petroleum ether/EtOAc=3/1). Yield: 235 mg, 76%.

$^1$H-NMR (CDCl$_3$): δ:7.6 (d, 1H), 7.4 (m, 6H), 7.1 (s, 1H), 5.1 (s, 2H), 4.5 (s, 2H), 4.0 (m, 2H), 2.8 (m, 2H).

7-(Trifluoromethoxy)-2,3,4,5-tetrahydrobenzo[f][1,4]thiazepine hydrobromide (31)

The starting material 30 (200 mg) was treated with 3 mL of HBr/AcOH solution for 1 h. To the reaction mixture was added diethyl ether (20 mL). The white solid was filtered to give the title compound as HBr salt. Yield: 182 mg.

$^1$H-NMR (300 MHz, CD$_3$OD): δ:7.8 (d, 1H), 7.5 (s, 1H), 7.3 (d, 1H), 4.6 (s, 2H), 3.7 (m, 2H), 3.0 (m, 2H).

MS: 250 (M+1).

Example 15

Synthesis of 1-(7-methoxy-2,3-dihydrobenzo[f][1,4]thiazepin-4(5H)-yl)prop-2-en-1-one (33) (Scheme 16)

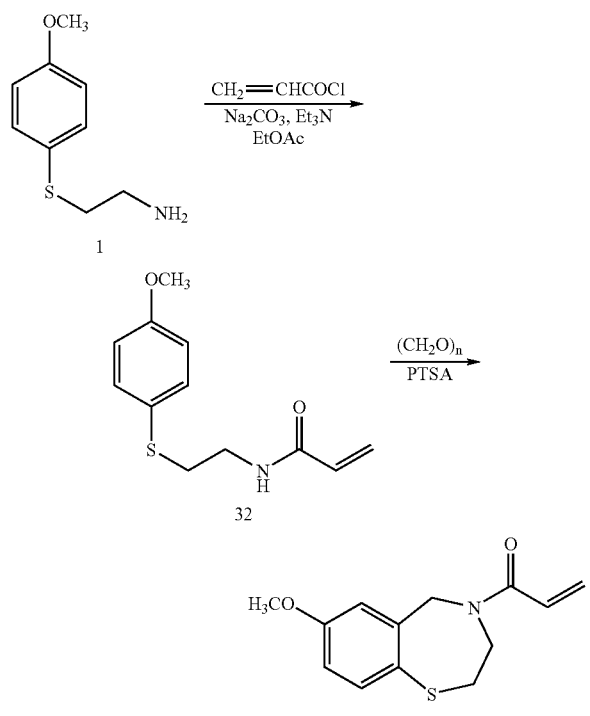

N-(2-(4-Methoxyphenylthio)ethyl)acrylamide (32)

To a solution of compound 1 (1.83 g) in EtOAc (50 mL) was added acryloyl chloride (1.35 g, 1.5 eq.) and Na$_2$CO$_3$ (2.12 g, 2.0 eq.). The reaction mixture was stirred at r.t. overnight and triethylamine was added. After stirring for 20 min, the mixture was washed with H$_2$O (20 mL), 1N HCl (2×20 mL) and sat. NaHCO$_3$ (2×20 mL). The solvents were removed by evaporation under reduced pressure to give product 32 as white solid (one spot on TLC). Yield: 2.2 g, 92.8%.

$^1$H-NMR (300 MHz, CDCl$_3$): δ:7.4 (d, 2H), 6.8 (d, 2H), 6.3 (d, 1H), 6.1 (dd, 1H), 5.95 (broad, 1H, NH), 5.6 (d, 1H), 3.8 (s, 3H), 3.5 (m, 2H), 3.0 (t, 2H).

1-(7-Methoxy-2,3-dihydrobenzo[f][1,4]thiazepin-4(5H)-yl)prop-2-en-1-one (33)

A mixture of compound 32 (280 mg), paraformaldehyde (600 mg), p-toluenesulfonic acid (140 mg) in benzene (7.0 mL) was stirred at 80° C. for 16 h. The reaction mixture was filtered and washed with sat. NaHCO$_3$ solution (2×3 mL). The solvents were removed by evaporation under reduced pressure to give product 33 as an oil. Yield: 253 mg, 86%.

$^1$H-NMR (300 MHz, CDCl$_3$): δ:7.4 (m, 1H), 7.1 (s, 1H), 6.8 (m, 1H), 6.5 (dd, 1H), 6.3 (m, 1H), 5.7 (dd, 1H), 4.7 (s, 2H), 4.0 (s, broad, 2H), 3.8 (s, 3H), 2.8 (m, 2H).

Example 16

Synthesis of 7-methoxy-1,2,11,11a-tetrahydrobenzo[f]pyrrolo[2,1-c][1,4]thiazepin-3(5H)-one (35) (Scheme 17)

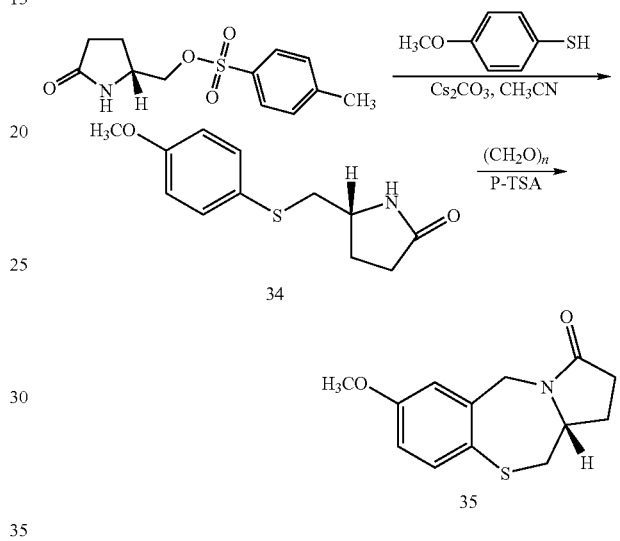

(R)-5-((4-methoxyphenylthio)methyl)pyrrolidin-2-one (34)

To a solution of (R)-(5-oxopyrrolidin-2-yl)methyl 4-methylbenzenesulfonate (Helvetica Chimica Acta 1990, 73, 122-32; Tetrahedron: Asymmetry 2007, 18, 664-670) (1.05 g, 3.9 mmol) in CH$_3$CN (30 mL) was added 4-methoxybenzenthiol (0.55 g, 3.9 mmol) and Cs$_2$CO3 (5 g, excess). The reaction mixture was stirred for 3 days. To the solution was added EtOAc (50 mL) and H$_2$O (30 ml). The organic phase was separated. The solvents were removed by evaporation to give the title compound as an oil (0.91 g, 98%). TLC and NMR indicated that the product was pure enough for the next step.

$^1$H-NMR (300 MHz, CDCl$_3$): δ:7.4 (d, 2H), 6.8 (d, 2H), 6.19 (s, br, 1H), 3.8 (s, 3H), 3.7 (m, 1H), 3.0 (dd, 1H), 2.8 (dd, 1H), 2.3 (m, 3H), 1.80 (m, 1H).

7-Methoxy-1,2,11,11a-tetrahydrobenzo[f]pyrrolo[2,1-c][1,4]thiazepin-3(5H)-one (35)

A mixture of 5-((4-methoxyphenylthio)methyl)pyrrolidin-2-one (34) (160 mg), paraformaldehyde (2.0 g), p-toluenesulfonic acid (200 mg) in benzene (60 mL) was stirred at 80° C. for 18 h. The reaction mixture was filtered and washed with sat. NaHCO$_3$ solution (2×10 mL). The solvents were removed by evaporation under reduced pressure to give crude product 34 as an oil. The product was purified by chromatography on SiO$_2$ (CH$_2$Cl$_2$/EtOAc=5/1). Yield: 140 mg, 87.5%.

$^1$H-NMR (300 MHZ, CDCl$_3$): δ:7.45 (d, 1H), 7.05 (s, 1H), 6.7 (d, 1H), 4.95 (d, 1H), 4.6 (d, 1H), 4.0 (m, 1H), 3.8 (s, 3H), 2.9 (d, 1H), 2.6 (d, 1H), 2.4 (m, 2H), 2.3 (m, 1H), 1.6 (m, 1H).

Example 17

Synthesis of Compound 402-(7-methoxy-2,3-dihydrobenzo[f][1,4]thiazepin-4(5H)-yl)acetic acid (ARM111)) (Scheme 18)

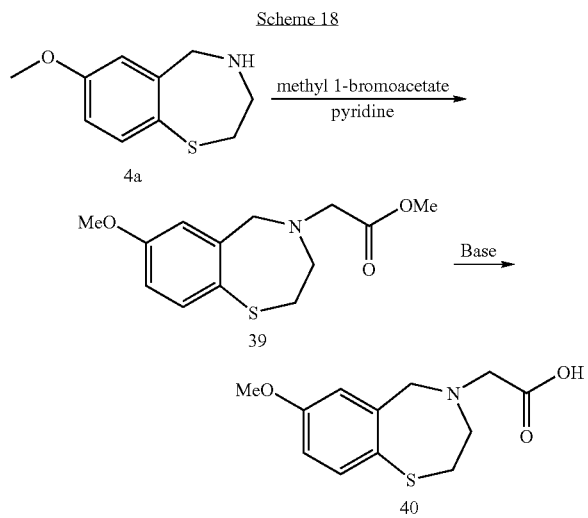

Compound 1 is converted into compound 4 or its free base 4a as described in Example 1. To prepare compound 40, a mixture of compound 4 or its free base 4a, methyl 1-bromoacetate and pyridine are reacted in DMF for a suitable amount of time. To this mixture, ethyl acetate is added, and if necessary, the reaction mixture is washed with a basic solution (for example NaHCO$_3$), or water. The product compound 39 (ARM110), as an oil, may be purified, for example by SiO$_2$ column chromatography. Then, a base (such as 1N NaOH) is added to compound 39 in a solvent (such as MeOH), and the mixture is allowed to react for a suitable amount of time. The solvents are then removed, for example under reduced pressure, and the residue may then be dissolved in an aqueous solution, such as water. The aqueous phase may be washed with ethyl acetate and acidified, for example with 1N HCl, to pH of around 4. The solvents may then be removed, for example under reduced pressure, to produce crude 40. The NaCl may be removed using an alcohol, such as ethanol, to yield pure 40 as a solid.

The invention is not to be limited in scope by the specific embodiments described herein. Indeed, various modifications within the spirit and scope of the invention in addition to those described herein will become apparent to those skilled in the art from the foregoing description. Such modifications are intended to fall within the scope of the described invention.

What is claimed is:

1. A process for preparing a 2,3,4,5-tetrahydro[1,4]benzothiazepine of formula:

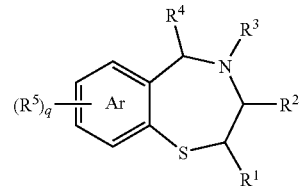

which comprises reacting a [2-(acylaminoethyl)thio]arene of formula

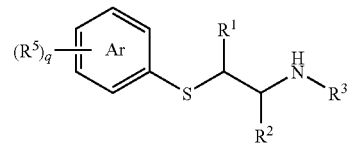

with an aldehyde of formula R$^4$CHO or an oligomer or polymer thereof, and with an acid, wherein:

Ar is phenyl;

R$^1$, R$^2$ and R$^4$ are each independently H, (C$_1$-C$_6$)alkyl, cycloalkyl, aryl, heterocyclyl, heteroaryl, (C$_1$-C$_6$)alkyl-aryl, (C$_1$-C$_6$)alkyl-cycloalkyl, (C$_1$-C$_6$)alkyl-heterocyclyl or (C$_1$-C$_6$)alkyl-heteroaryl, each of the aryl, cycloalkyl, heterocyclyl and heteroaryl optionally substituted with one to three substituents independently selected from the group consisting of halogen, alkyl, alkoxyl, nitro, cyano and haloalkyl;

R$^3$ is (C$_1$-C$_{10}$)acyl; P(O)R$^8$R$^9$, C(=O)—R$^{10}$, C(=S)—R$^{11}$, S(=O)$_2$R$^{12}$, (CH$_2$)$_m$R$^{13}$, an amine protecting group, OH, (C$_1$-C$_6$)alkyl, cycloalkyl, aryl, heterocyclyl, heteroaryl, (C$_1$-C$_6$) alkyl-aryl, (C$_1$-C$_6$)alkyl-cycloalkyl, (C$_1$-C$_6$)alkyl-heterocyclyl or (C$_1$-C$_6$)alkyl-heteroaryl, each of the aryl, cycloalkyl, heterocyclyl and heteroaryl optionally substituted with one to three substituents independently selected from the group consisting of halogen, alkyl, alkoxyl, nitro, cyano and haloalkyl;

R$^5$ is chosen independently in each of its occurrences as H, (C$_1$-C$_6$) alkyl, cycloalkyl, aryl, heterocyclyl, heteroaryl, (C$_1$-C$_6$)alkyl-aryl, (C$_1$-C$_6$)alkyl-cycloalkyl, (C$_1$-C$_6$) alkyl-heterocyclyl, (C$_1$-C$_6$)alkyl-heteroaryl, halogen, acyl, SO$_3$, —OR$^6$, —SR$^6$, —NR$^{6a}$R$^{6b}$, —N(R$^6$)C(=O) OR$^7$, N(R$^6$)C(=O)R$^7$, —C(=O)NR$^{6a}$R$^{6b}$, —C(=O) OR$^6$, —C(=O)R$^6$, —OC(=O)R$^6$, —NO$_2$, —CN, —(C$_1$-C$_6$)haloalkyl, —O—(C$_1$-C$_6$)haloalkyl, —N$_3$ or —P(O)R$^8$R$^9$, each of the aryl, cycloalkyl, heterocyclyl and heteroaryl optionally substituted with one to three substituents independently selected from the group consisting of halogen, alkyl, alkoxyl, nitro, cyano and haloalkyl;

R$^{10}$ and R$^{11}$ are each independently H, —OR$^{14}$, —NR$^{6a}$R$^{6b}$, NHNHR$^{15}$, NHOH, CONH$_2$NHR$^{15}$, CO$_2$R$^{15}$, CONR$^{15}$, halogen, alkoxy, aryloxy, allyloxy, benzyloxy, substituted benzyloxy, fluoroenylmethoxy, adamantyloxy, (C$_1$-C$_6$)alkyl, cycloalkyl, aryl, heterocyclyl, heteroaryl, (C$_1$-C$_6$)alkyl-aryl, (C$_1$-C$_6$)alkyl-cycloalkyl, (C$_1$-C$_6$)alkyl-heterocyclyl or (C$_1$-C$_6$)alkyl-heteroaryl, each of the aryl, cycloalkyl, heterocyclyl and heteroaryl optionally substituted with one to three substituents independently selected from the group consisting of halogen, alkyl, alkoxyl, nitro, cyano and haloalkyl;

$R^6$, $R^{6a}$, $R^{6b}$, $R^7$, $R^8$, $R^9$, $R^{12}$, $R^{14}$ and $R^{17}$ are each independently at each of their occurrences H, —$OR^{15}$, —$NR^{15}R^{16}$, $NHNHR^{16}$, NHOH, ($C_1$-$C_6$)alkyl, cycloalkyl, aryl, heterocyclyl, heteroaryl, ($C_1$-$C_6$)alkyl-aryl, ($C_1$-$C_6$)alkyl-cycloalkyl, ($C_1$-$C_6$)alkyl-heterocyclyl or ($C_1$-$C_6$)alkyl-heteroaryl, each of the aryl, cycloalkyl, heterocyclyl and heteroaryl optionally substituted with one to three substituents independently selected from the group consisting of halogen, alkyl, alkoxyl, nitro, cyano and haloalkyl, or $R^{6a}$ and $R^{6b}$, together with the nitrogen to which they are attached, represent a 5, 6, or 7-membered ring nitrogen-containing heterocycle;

$R^{15}$ and $R^{16}$ are each independently at each of their occurrences H, NHOH, ($C_1$-$C_6$)alkyl, cycloalkyl, aryl, heterocyclyl, heteroaryl, ($C_1$-$C_6$)alkyl-aryl, ($C_1$-$C_6$)alkyl-cycloalkyl, ($C_1$-$C_6$)alkyl-heterocyclyl or ($C_1$-C)alkyl-heteroaryl, each of the aryl, cycloalkyl, heterocyclyl and heteroaryl optionally substituted with one to three substituents independently selected from the group consisting of halogen, alkyl, alkoxyl, nitro, cyano and haloalkyl;

$R^{13}$ is $NH_2$, OH, —$SO_2R^{16}$, —$NHSO_2R^{16}$, C(=O)$R^{17}$, NH(C=O)$R^{17}$, —O(C=O)$R^{17}$, or —P(O)$R^8R^9$; m is an integer from 1-10; and q is zero or an integer from 1-4, provided that when $R^5$ is —C(=O)$R^6$, $R^5$ is not in an ortho position relative to the sulfur side chain.

2. The process according to claim 1, wherein the [2-(acylaminoethyl)thio]arene is first reacted with the aldehyde or an oligomer or polymer thereof and a base to form an [N-hydroxymethyl-2-[acylaminoethyl)thio]arene of formula

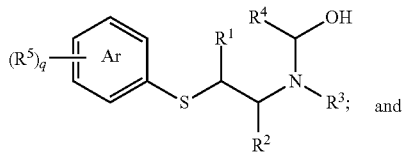

the [N-hydroxymethyl-2-(acylaminoethyl)thio]arene is then treated with the acid to form the 2,3,4,5-tetrahydro[1,4]benzothiazepine wherein the acid is a sulfonic acid or a Lewis acid.

3. The process according to claim 2, wherein the base is an alkali metal hydride, hydroxide or carbonate, pyridine, or a trialkylamine.

4. The process according to claim 3, wherein the base is NaH, NaOH, KOH, $Na_2CO_3$, $K_2CO_3$, $Cs_2CO_3$, $Et_3N$ or $(iPr)_2$NEt.

5. The process according to claim 1, wherein the acid is a sulfonic acid or a Lewis acid.

6. The process according to claim 5, wherein the sulfonic acid is selected from the group consisting of toluenesulfonic acid, benzenesulfonic acid, methanesulfonic acid, pyridinium p-toluenesulfonate, and trifluoromethanesulfonic acid, and the Lewis acid is selected from the group consisting of boron trifluoride etherate, titanium tetrachloride, aluminum chloride and zinc chloride.

7. The process according to claim 1, wherein the aldehyde or an oligomer or polymer thereof is formaldehyde, paraformaldehyde or 1,3,5-trioxane.

8. The process according to claim 1, wherein $R^3$ is acetyl, benzoyl, toluoyl, benzyloxycarbonyl, t-butoxycarbonyl, acryloyl, oxalyl or —C(=O)N($R^{19})_2$, wherein each $R^{19}$ is hydrogen, ($C_1$-$C_6$)alkyl, aryl, heterocyclyl, heteroaryl, ($C_1$-$C_6$)alkylaryl, ($C_1$-$C_6$)alkylheterocyclyl, or ($C_1$-$C_6$)alkylheteroaryl, or taken together, N($R^{19})_2$ represents a 5, 6, or 7-membered ring nitrogen-containing heterocycle.

9. The process according to claim 1, wherein:
$R^5$ is ($C_1$-$C_6$)alkyl, aryl, heterocyclyl, heteroaryl, halogen, —$OR^6$, —$SR^6$, —$NO_2$, —CN, —($C_1$-$C_4$)haloalkyl or —O—($C_1$-$C_4$)haloalkyl; and $R^6$ is H or ($C_1$-$C_6$)alkyl.

10. The process according to claim 1, wherein
q is 0 or 1; $R^1$, $R^2$ and $R^4$ are hydrogen;
$R^3$ is ($C_1$-$C_{10}$)acyl of formula —C(=O)—$R^{18}$, or an amine protecting group, wherein $R^{18}$ is H, ($C_1$-$C_6$)alkyl, ($C_1$-$C_6$)alkoxy, allyloxy, benzyloxy, substituted benzyloxy, fluorenylmethoxy or adamantyloxy;
$R^5$ is H, ($C_1$-$C_6$)alkyl, halogen, —$OR^6$, —$SR^6$, —$NO_2$, —CN, —($C_1$-$C_4$)haloalkyl or —O—($C_1$-$C_4$)haloalkyl,
$R^6$ is H or ($C_1$-$C_6$)alkyl; and the process further comprises converting a compound of formula

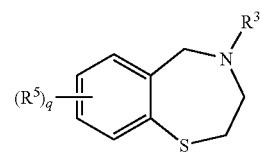

to an oxalate compound of formula

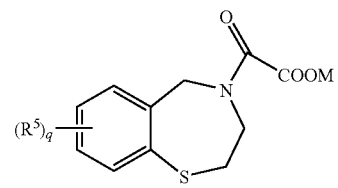

wherein M is H, ammonium, an alkali metal or an alkaline earth metal.

11. The process according to claim 10, wherein the conversion step comprises
cleaving the $R^3$ group to provide a 2,3,4,5-tetrahydrobenzo[f][1,4]thiazepine of formula:

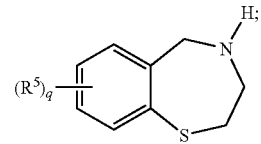

acylating 2,3,4,5-tetrahydrobenzo[f][1,4]thiazepine with an oxalate ester; and
hydrolyzing the ester.

12. The process according to claim 11, wherein the hydrolysis step comprises treating the ester with a base of an alkali metal hydride, hydroxide or carbonate, pyridine, or a trialkylamine and, optionally when M is H, acidifying.

13. The process according to claim 12, wherein the base is NaH, NaOH, KOH, $Na_2CO_3$, $K_2CO_3$, $Cs_2CO_3$, $Et_3N$ or $(iPr)_2$NEt.

14. The process according to claim 11, which further comprises converting the oxalate compound wherein M is H into a salt thereof, wherein M is a cation selected from $Na^+$, $Mg^{++}$, $Ca^{++}$ and ammonium.

15. The process according to claim 11, wherein q is 1 and $R^5$ is $OCH_3$ at position 7 of the benzothiazepine ring, and the compound has the formula

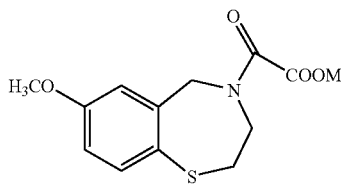

wherein M is hydrogen, ammonium, an alkali metal or an alkaline earth metal.

16. The process according to claim 15, for specifically preparing a compound of the formula

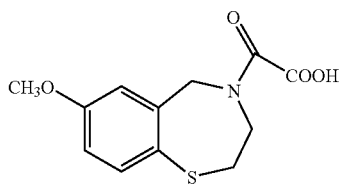

wherein the [2-(acylaminoethyl)thio]arene has the formula

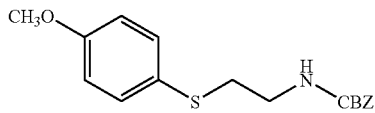

the aldehyde is paraformaldehyde and the acid is toluenesulfonic acid or hydrochloric acid and the reaction provides a CBZ-protected benzothiazepine of formula

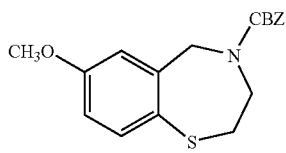

and the method further comprises:
cleaving carbobenzyloxy group with acid to provide 7-methoxy-2,3,4,5-tetrahydrobenzo[f][1,4]thiazepine;
acylating the 7-methoxy-2,3,4,5-tetrahydrobenzo[f][1,4]thiazepine with methyl chlorooxalate;
hydrolyzing the methyl ester with aqueous base;
acidifying to form the acid compound; and
optionally converting the acid compound to a compound of formula

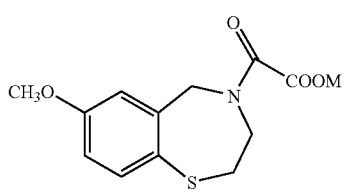

wherein M is ammonium, an alkali metal or an alkaline earth metal.

17. The process according to claim 1, wherein $R^3$ is $R^{3a}$, and the 2,3,4,5-tetrahydro[1,4]benzothiazepine is prepared by treating a [2-(acylaminoethyl)thio]arene of formula

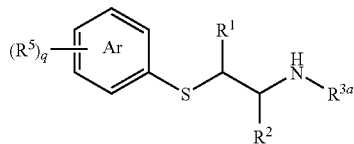

with an aldehyde of formula $R^4CHO$ or an oligomer or polymer thereof, and an acid to produce a compound of formula

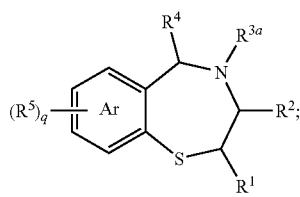

wherein $R^{3a}$ is $(C_1-C_{10})$acyl of formula $—C(=O)—R^{18}$ or an amine protecting group, wherein $R^{18}$ is H, $(C_1-C_6)$ alkyl, $(C_1-C_6)$alkoxy, allyloxy, benzyloxy, substituted benzyloxy, fluorenylmethoxy or adamantyloxy.

18. The process according to claim 17, which further comprises cleaving $R^{3a}$ to produce a 4-unsubstituted-2,3,4,5-tetrahydrobenzo[f][1,4]thiazepine of formula

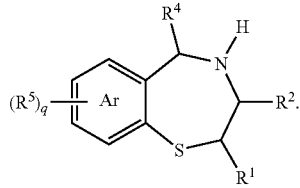

19. The process according to claim 18, which further comprises acylating the 4-unsubstituted-2,3,4,5-tetrahydrobenzo[f][1,4]thiazepine with $R^3X$ to produce a compound of formula

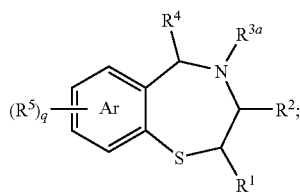

wherein
$R^3$ is $(C_1-C_{10})$acyl; $P(O)R^8R^9$, $C(=O)—R^{10}$, $C(=S)—R^{11}$, $S(=O)_2R^{12}$, $(CH_2)_mR^{13}$, an amine protecting group, OH, $(C_1-C_6)$alkyl, cycloalkyl, aryl, heterocyclyl, heteroaryl, $(C_1-C_6)$alkyl-aryl, $(C_1-C_6)$alkyl-cycloalkyl, $(C_1-C_6)$alkyl-heterocyclyl or $(C_1-C_6)$alkyl-heteroaryl, each of the aryl, cycloalkyl, heterocyclyl and heteroaryl optionally substituted with one to three substituents independently selected from the group consisting of halogen, alkyl, alkoxyl, nitro, cyano and haloalkyl; and
X is halogen, $(C_1-C_{10})$acyloxy, or an activated ester residue.

20. The process according to claim 18, which further comprises reacting the 4-unsubstituted-2,3,4,5-tetrahydrobenzo

[f][1,4]thiazepine to with a compound of formula X—CH2—COOR' wherein X is a halogen and R' is an alkyl to form an ester compound of formula:

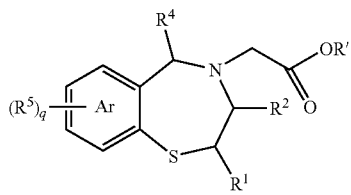

and hydrolyzing the ester to form a compound of formula:

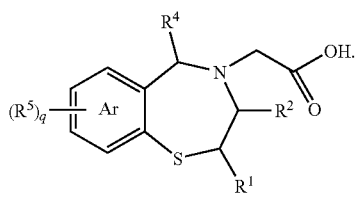

21. The process according to claim 17, wherein $R^{3a}$ is t-butoxycarbonyl, benzyloxycarbonyl, substituted benzyloxycarbonyl or fluorenylmethoxycarbonyl.

22. The process according to claim 17, wherein the method further comprises treating a compound of formula

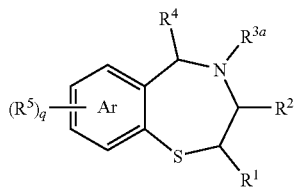

wherein $R^{3a}$ is —C(=O)—$R^{18}$ wherein $R^{18}$ is ($C_1$-$C_4$) alkoxy, allyloxy, benzyloxy, substituted benzyloxy, fluorenylmethoxy or adamantyloxy, with an amine of formula $HN(R^{19})_2$, wherein each $R^{19}$ is hydrogen, ($C_1$-$C_6$)alkyl, aryl, heterocyclyl, heteroaryl, ($C_1$-$C_6$)alkylaryl, ($C_1$-$C_6$)alkylheterocyclyl, or ($C_1$-$C_6$)alkylheteroaryl, or taken together, $N(R^{19})_2$ represents a 5, 6, or 7-membered ring nitrogen-containing heterocycle, to form a compound of formula:

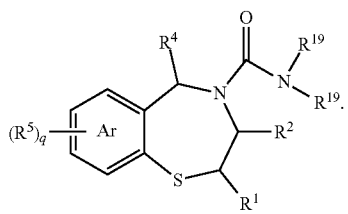

23. The process according to claim 17, wherein the [2-(acylaminoethyl)thio]arene compound has the formula

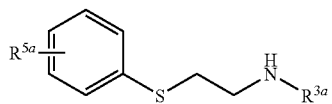

and is reacted with
(i) the formaldehyde and an acid to form a protected benzothiazepine of the formula:

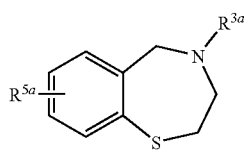

or
(ii) the formaldehyde and a base to form an [N-hydroxymethyl-2-(acylaminoeth1)thio]benzene of formula;

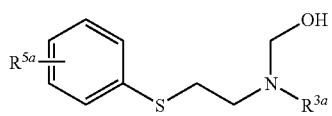

and
the [N-hydroxymethyl-2-(acylaminoethl)thio]benzene is further reacted with an acid to provide a protected benzothiazepine of the formula

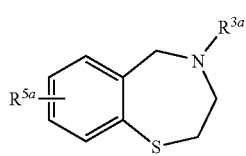

wherein:
$R^{3a}$ is ($C_1$-$C_{10}$)acyl of formula —C(=O)—$R^{18}$ or an amine protecting group;
$R^{5a}$ is H, ($C_1$-$C_6$)alkyl, halogen, —$OR^6$, —$SR^6$, —$NO_2$, —CN, —($C_1$-$C_4$)haloalkyl or —O—($C_1$-$C_4$)haloalkyl;
$R^6$ is H or ($C_1$-$C_6$)alkyl; and
$R^{18}$ is H, ($C_1$-$C_6$)alkyl, ($C_1$-$C_4$)alkoxy, allyloxy, benzyloxy, substituted benzyloxy, fluorenylmethoxy or adamantyloxy.

24. The process according to claim 23, further comprising the step of cleaving the $R^{3a}$ group to obtain a compound of formula

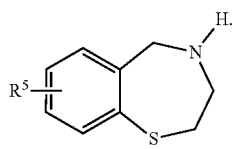

25. The process according to claim 24, further comprising the step of acylating the 4-unsubstituted 2,3,4,5-tetrahydrobenzo[f][1,4]benzothiazeine with $R^3X$ to obtain a compound of formula

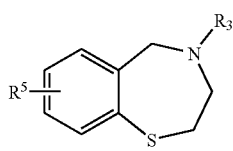

wherein
R³ is (C₁-C₁₀)acyl; P(O)R⁸R⁹, C(=O)—R¹⁰, C(=S)—R¹¹, S(=O)₂R¹², (CH₂)ₘR¹³, an amine protecting group, OH, (C₁-C₆)alkyl, cycloalkyl, aryl, heterocyclyl, heteroaryl, (C₁-C₆)alkyl-aryl, (C₁-C₆)alkyl-cycloalkyl, (C₁-C₆)alkyl-heterocyclyl or (C₁-C₆)alkyl-heteroaryl, each of the aryl, cycloalkyl, heterocyclyl and heteroaryl optionally substituted with one to three substituents independently selected from the group consisting of halogen, alkyl, alkoxyl, nitro, cyano and haloalkyl; and
X is halogen, (C₁-C₁₀)acyloxy, or an activated ester residue.

26. The process according to claim 23, which further comprises converting

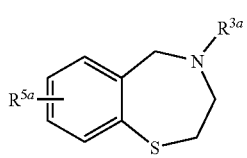

to

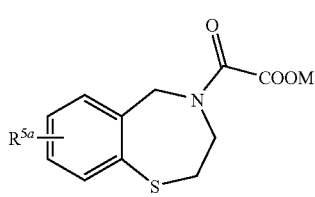

wherein M is H, ammonium, an alkali metal or an alkaline earth metal.

27. The process according to claim 26, wherein:
the converting is accomplished by cleaving the R³ᵃ group to provide a 2,3,4,5-tetrahydrobenzo[f][1,4]thiazepine, acylating the 2,3,4,5-tetrahydrobenzo[f][1,4]thiazepine with an oxalate ester, and hydrolyzing the ester; and/or
the hydrolysis step comprises treating the ester with a base and, optionally, when M is H, acidifying, wherein the base is an alkali metal hydride, hydroxide or carbonate, pyridine, or a trialkylamine, and optionally converting the resulting product wherein M is H into a salt thereof, wherein M is a cation.

28. The process according to claim 1, which further comprises preparing the [2-(acylaminoethyl)thio]arene by reacting a compound of formula

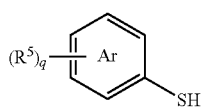

with a compound of formula

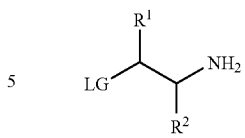

to provide a compound of formula

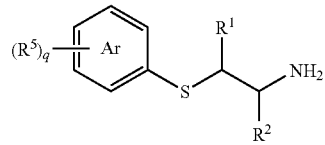

optionally in the presence of a base followed by reaction with a compound of formula R³X, wherein LG is a leaving group for nucleophilic displacement by thiol and X is a leaving group for nucleophilic displacement by an amine.

29. The process according to claim 28, wherein LG is a halogen or a sulfonate, the base is an alkali metal hydride, hydroxide or carbonate, pyridine or a trialkylamine and R³X is an acid chloride, an acid anhydride, an activated ester, a chloroformate or a carbamic chloride; wherein the sulfonate is selected from the group consisting of methanesulfonate, toluenesulfonate, benzenesulfonate, tri fluoromethanesulfonate, nitrophenylsulfonate and bromophenylsulfonate, and wherein the halogen is selected from the group consisting of chloro, iodo and bromo.

30. The process according to claim 1, wherein the [2-(acylaminoethyl)thio]arene is prepared by:
reacting a compound of formula

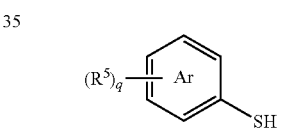

with a compound of formula

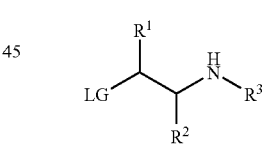

optionally in the presence of a base, wherein LG is a leaving group for nucleophilic displacement by a thiol.

31. The process according to claim 30, wherein LG is a halogen or a sulfonate and the base is an alkali metal hydride, hydroxide or carbonate, pyridine or a trialkylamine, wherein the sulfonate is selected from the group consisting of methanesulfonate, toluenesulfonate, benzenesulfonate, trifluoromethanesulfonate, nitrophenylsulfonate and bromophenylsulfonate, and wherein the halogen is selected from the group consisting of chloro, iodo and bromo.

32. The process according to claim 1, wherein R¹, R² and R⁴ are hydrogen.

33. The process according to claim 19, wherein R³X is an acid chloride, an acid anhydride, an activated ester, a chloroformate or a carbamic chloride.

* * * * *

UNITED STATES PATENT AND TRADEMARK OFFICE
CERTIFICATE OF CORRECTION

PATENT NO. : 8,618,282 B2
APPLICATION NO. : 12/397212
DATED : December 31, 2013
INVENTOR(S) : Shixian Deng et al.

It is certified that error appears in the above-identified patent and that said Letters Patent is hereby corrected as shown below:

Title Page, (73) Assignee: Please add Assignee "ARMGO Pharma, Inc., Tarrytown, New York"

Title Page, (56) Other Publication, second column, line 17: "Cataluzed" should be: -- Catalyzed --

Title Page, ABSTRACT:

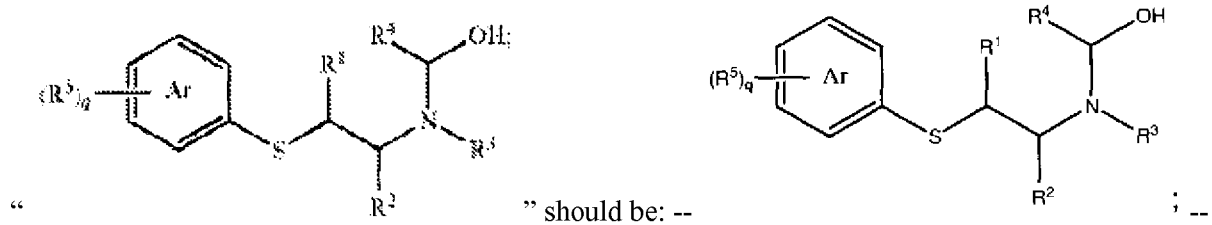

In the Specification

Column 15, line 47:

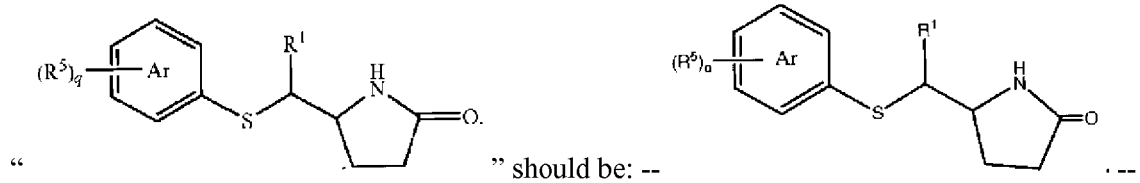

Column 19, line 5:

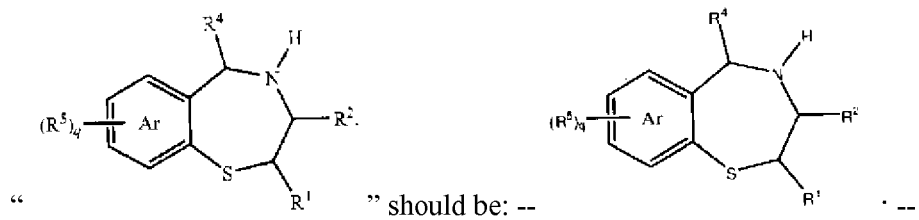

Signed and Sealed this
Thirteenth Day of May, 2014

Michelle K. Lee
*Deputy Director of the United States Patent and Trademark Office*

CERTIFICATE OF CORRECTION (continued)
U.S. Pat. No. 8,618,282 B2

Column 19, line 20:

" 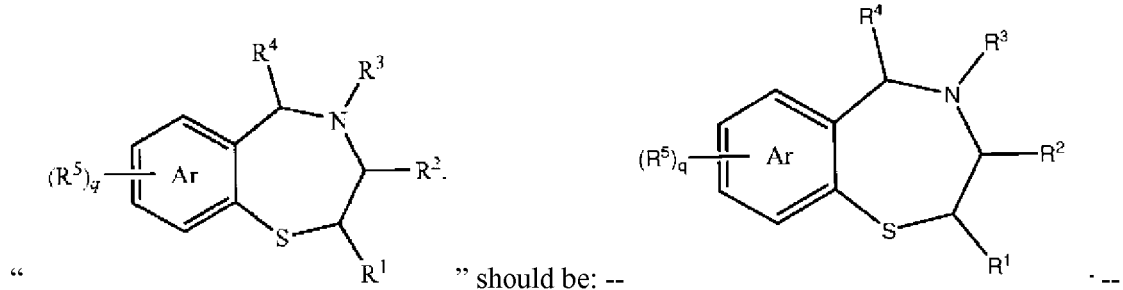 " should be: -- 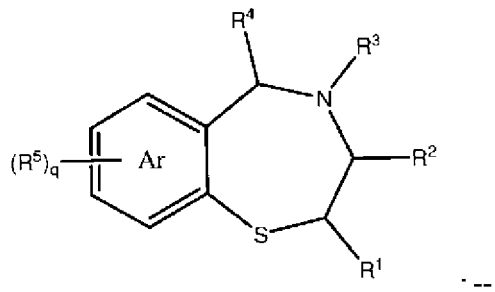 --

Column 23, line 47:

" 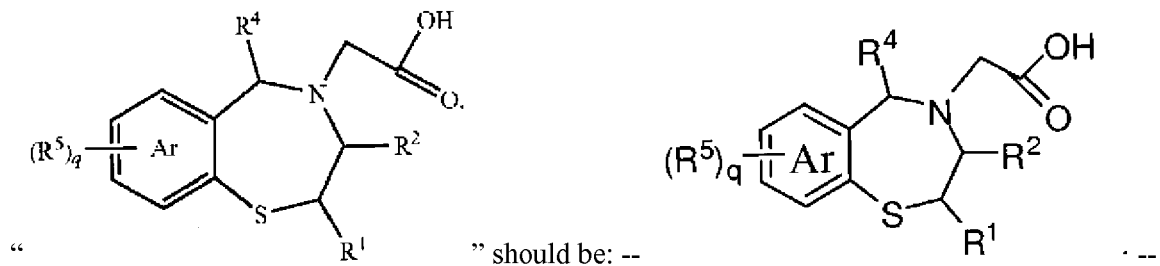 " should be: -- 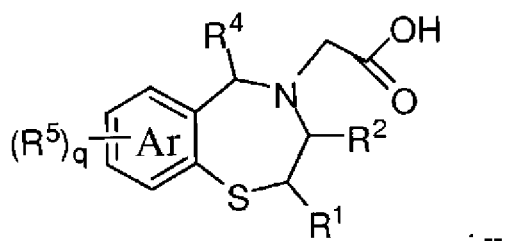 --

Column 42, line 46: "CS2CO3" should be: -- $CS_2CO_3$ --

Column 45, line 17: "$(C_1-C)$" should be: -- $(C_1-C_6)$ --

In the Claims

Column 45, line 37, Claim 2:

" 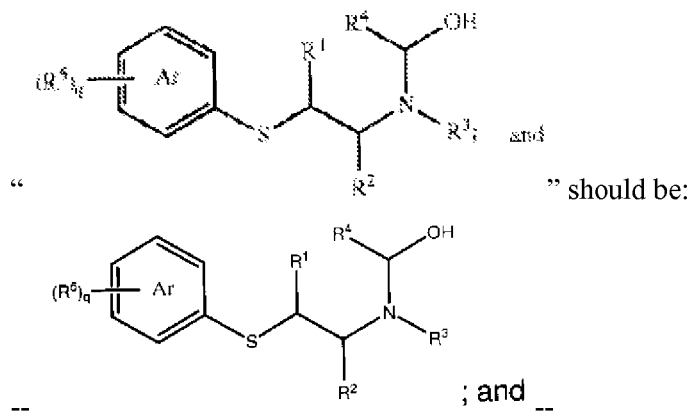 " should be:

-- ; and --

CERTIFICATE OF CORRECTION (continued)
U.S. Pat. No. 8,618,282 B2

Column 46, line 50, Claim 11:

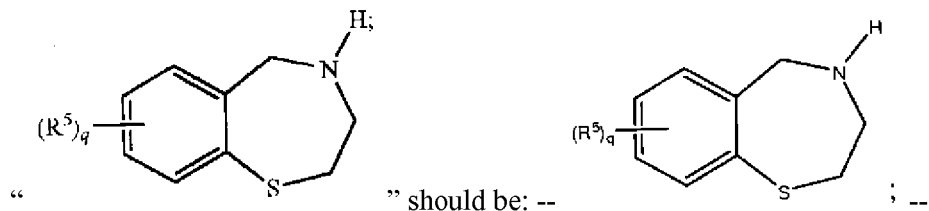

" " should be: --

Column 47, line 17:

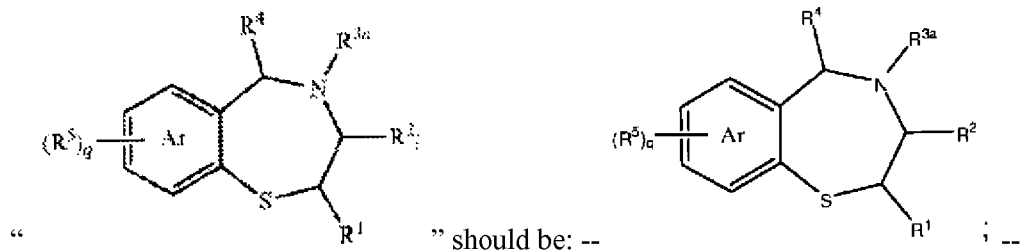

" " should be: --

Column 48, line 35:

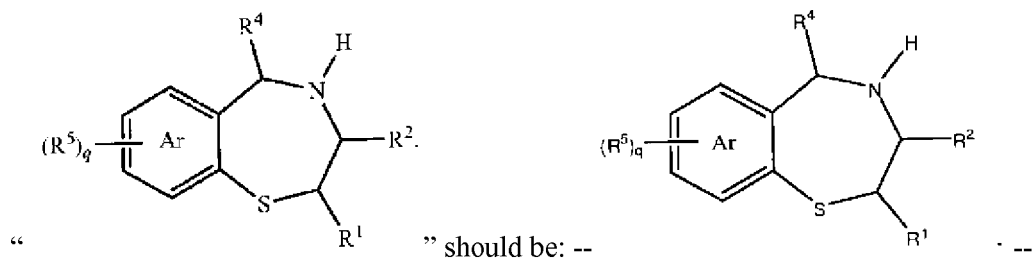

" " should be: --

Column 48, line 50, Claim 19:

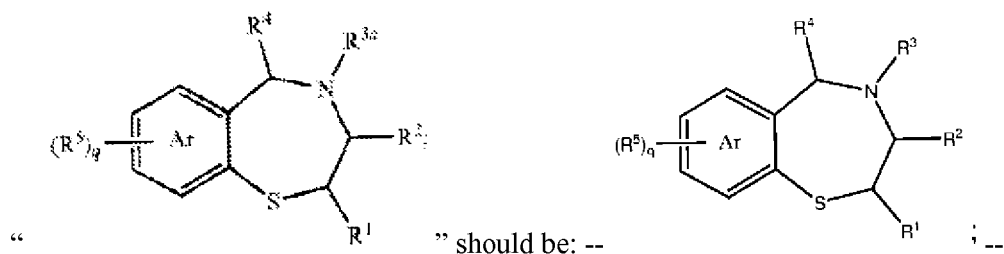

" " should be: --

Column 49, line 1: "X-CH2-COOR'" should be: -- X-CH$_2$-COOR' --

Column 49, line 25, Claim 20:

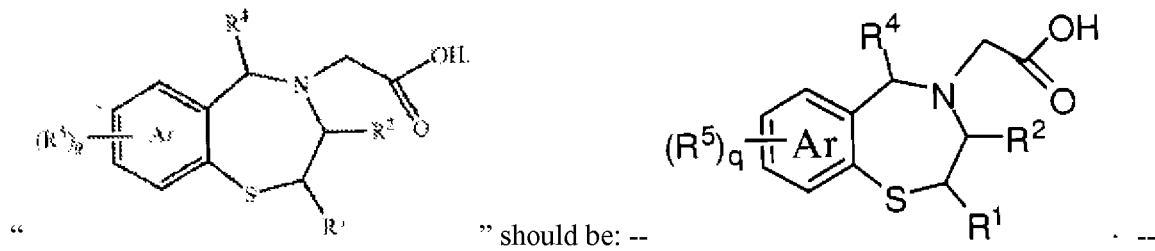

" " should be: --

CERTIFICATE OF CORRECTION (continued)
U.S. Pat. No. 8,618,282 B2

Page 4 of 4

Column 49, line 60, Claim 22:

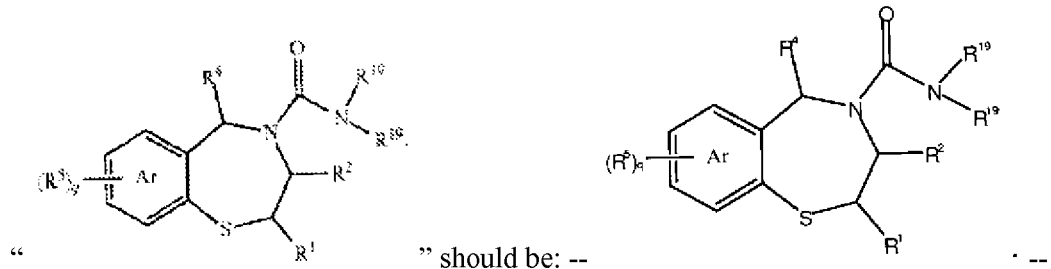

Column 50, line 60, Claim 24:

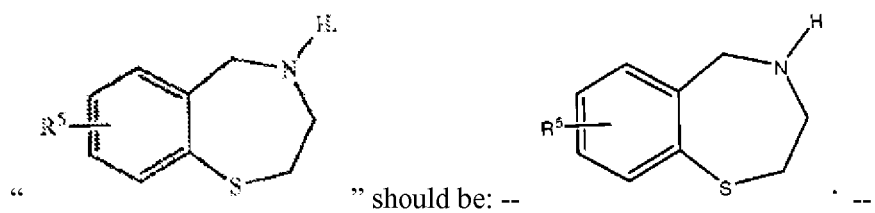

UNITED STATES PATENT AND TRADEMARK OFFICE
CERTIFICATE OF CORRECTION

PATENT NO.        : 8,618,282 B2
APPLICATION NO.   : 12/397212
DATED             : December 31, 2013
INVENTOR(S)       : Shixian Deng et al.

Page 1 of 1

It is certified that error appears in the above-identified patent and that said Letters Patent is hereby corrected as shown below:

Title Page,
Item [73], Assignee "ARMGO Pharma, Inc., Tarrytown, New York" (as added in the Certification of Correction issued May 13, 2014) is deleted and Assignee should appear as printed on the title page of patent at issuance -- Les Laboratories Servier, Suresnes Cedex (FR) --.

Signed and Sealed this
First Day of July, 2014

Michelle K. Lee
*Deputy Director of the United States Patent and Trademark Office*

UNITED STATES PATENT AND TRADEMARK OFFICE
CERTIFICATE OF CORRECTION

PATENT NO.           : 8,618,282 B2                                    Page 1 of 1
APPLICATION NO.      : 12/397212
DATED                : December 31, 2013
INVENTOR(S)          : Shixian Deng et al.

It is certified that error appears in the above-identified patent and that said Letters Patent is hereby corrected as shown below:

Title Page: Please add Assignee "ARMGO Pharma, Inc., Tarrytown, New York"

Signed and Sealed this
Twenty-ninth Day of July, 2014

Michelle K. Lee
*Deputy Director of the United States Patent and Trademark Office*